(12) United States Patent
Urano et al.

(10) Patent No.: US 7,672,429 B2
(45) Date of Patent: Mar. 2, 2010

(54) RADIOTHERAPY DEVICE CONTROL APPARATUS AND RADIATION IRRADIATION METHOD

(75) Inventors: Susumu Urano, Hiroshima (JP); Shuji Kaneko, Hiroshima (JP); Noriyuki Kawada, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 305 days.

(21) Appl. No.: 11/705,494

(22) Filed: Feb. 13, 2007

(65) Prior Publication Data

US 2007/0211856 A1    Sep. 13, 2007

(30) Foreign Application Priority Data

Mar. 10, 2006    (JP)    ............................. 2006-065316

(51) Int. Cl.
*A61N 5/10*    (2006.01)
(52) U.S. Cl. ..................................................... 378/65
(58) Field of Classification Search .................... 378/65
See application file for complete search history.

(56) References Cited

U.S. PATENT DOCUMENTS

| | | | |
|---|---|---|---|
| 5,673,300 A | | 9/1997 | Reckwerdt et al. |
| 5,901,199 A | * | 5/1999 | Murphy et al. ................ 378/65 |
| 6,118,848 A | | 9/2000 | Reiffel |
| 6,125,164 A | * | 9/2000 | Murphy et al. ................ 378/65 |
| 6,148,060 A | * | 11/2000 | Collins et al. ................. 378/65 |
| 6,260,999 B1 | * | 7/2001 | Wofford et al. ............. 378/205 |
| 6,307,914 B1 | | 10/2001 | Kunieda et al. |
| 6,516,046 B1 | * | 2/2003 | Frohlich et al. ............... 378/65 |
| 6,842,502 B2 | * | 1/2005 | Jaffray et al. ................. 378/65 |
| 6,865,253 B2 | * | 3/2005 | Blumhofer et al. ............ 378/65 |
| 6,865,254 B2 | * | 3/2005 | Nafstadius ................... 378/65 |
| 6,888,919 B2 | * | 5/2005 | Graf ............................ 378/65 |
| 6,914,959 B2 | * | 7/2005 | Bailey et al. ................. 378/65 |
| 6,990,175 B2 | * | 1/2006 | Nakashima et al. ........... 378/65 |

(Continued)

FOREIGN PATENT DOCUMENTS

DE        197 28 788         1/1999

(Continued)

OTHER PUBLICATIONS

Japanese Office Action issued Dec. 16, 2008 for Japanese Patent Application No. 2006-065316 w/partial translation.

(Continued)

*Primary Examiner*—Allen C. Ho
(74) *Attorney, Agent, or Firm*—Wenderoth, Lind & Ponack L.L.P.

(57) ABSTRACT

A radiotherapy device control apparatus controls a radiotherapy device. The control apparatus includes a reference image creation section, a transmitted image creation section and an affected area position control section. The radiotherapy device includes a therapeutic radiation irradiation device that radiates therapeutic radiation, an imager that generates an image of a subject by using radiation transmitted through the subject, and a drive device that moves a couch, where the subject is arranged, with respect to the therapeutic radiation irradiation device. The affected area position control section judges whether a relative position of the couch with respect to the therapeutic radiation irradiation device is appropriate and changes the relative position of the couch by using the drive device based on a first position and a second position.

52 Claims, 5 Drawing Sheets

U.S. PATENT DOCUMENTS

| | | | |
|---|---|---|---|
| 7,227,925 B1 * | 6/2007 | Mansfield et al. | 378/65 |
| 7,239,684 B2 * | 7/2007 | Hara et al. | 378/65 |
| 7,412,086 B2 * | 8/2008 | Sakas et al. | 382/131 |
| 7,436,928 B2 * | 10/2008 | Urano et al. | 378/65 |
| 7,453,984 B2 * | 11/2008 | Chen et al. | 378/65 |
| 2003/0225325 A1 | 12/2003 | Kagermeier et al. | |
| 2005/0049478 A1 | 3/2005 | Kuduvalli et al. | |

FOREIGN PATENT DOCUMENTS

| | | |
|---|---|---|
| EP | 0 812 605 | 12/1997 |
| JP | 4-507048 | 12/1992 |
| JP | 3432268 | 10/1995 |
| JP | 8-511452 | 12/1996 |
| JP | 2000-140137 | 5/2000 |
| JP | 3053389 | 6/2000 |
| JP | 3326597 | 7/2000 |
| JP | 2001-259060 | 9/2001 |
| JP | 2002-331039 | 11/2002 |
| JP | 3394250 | 1/2003 |
| JP | 2003-220151 | 8/2003 |
| JP | 2004-121406 | 4/2004 |
| JP | 3746747 | 4/2004 |
| WO | 90/11721 | 10/1990 |
| WO | 92/06644 | 4/1992 |
| WO | 94/28971 | 12/1994 |
| WO | 99/35966 | 7/1999 |

OTHER PUBLICATIONS

European Office Action dated Oct. 1, 2009 for corresponding European Application No. 07 102 483.

* cited by examiner

RADIOTHERAPY DEVICE CONTROL APPARATUS AND RADIATION IRRADIATION METHOD

BACKGROUND OF THE INVENTION

1. Field of the Invention

The present invention relates to a radiotherapy device control apparatus and a radiation irradiation method, and more specifically to a radiotherapy device control apparatus and a radiation irradiation method for use in treating a patient by irradiating his or her affected area with radiation.

2. Description of the Related Art

Radiotherapy is known which treats a patient by irradiating his or her affected area (tumor) with radiation. It is desired that the radiotherapy provides a high therapeutic effect and that a dosage of radiation thereof irradiated to normal cells be smaller than a dosage of radiation irradiated to cells at the affected area.

The radiotherapy device is known which tracks a position of an affected area based on transmitted images photographed by applying diagnostic X-rays, and irradiates the position with a radiation for treatment. It is desired that a dosage of the diagnostic X-rays to a patient be as small as possible.

Japanese patent JP3746747B discloses a radiotherapy device capable of monitoring, in real time, condition of a treatment field even during radiation irradiation treatment. The radiotherapy device includes: a radiation irradiation head which irradiates a treatment field of a subject with therapeutic radiation; an X-ray source which irradiates the treatment field of the subject with diagnostic X-rays; a sensor array which detects transmitted X-rays of the diagnostic X-rays transmitted through the subject and then outputs them as diagnostic image data. The sensor array moves in conjunction with movement of the radiation irradiation head.

Japanese Laid Open Patent Application JP2004-121406A discloses a radiotherapy device capable of easily positioning, within a radiation irradiation range, a target to be irradiated with radiation. This radiotherapy device is characterized by being provided with: a radiation generator which emits radiation and laser beams concentrically with each other; a guide which moves the radiation generator along an orbit of a predetermined radius with respect to an isocenter serving as a center so that irradiation axes of the radiation and the laser beams emitted concentrically with each other intersect with each other at one point; a support member which rotates the guide around an inclined axis passing through the isocenter; a movable member which pivots the radiation generator by rotating axes intersecting with each other and moves along the guide; a detector which detects information of a transmitted image in a range including the isocenter and the target to be irradiated with the radiation arranged near the isocenter; an analyzer which calculates relative positional relationship between the isocenter and the target to be irradiated based on information of a plurality of the transmitted images respectively detected in a plurality of orientations by the detector and based on information of the orientations in which the transmitted images are detected with respect to the isocenter; and a controller which moves the radiation generator based on the relative positional relationship.

Japanese patent JP3053389B (corresponding to US6307914B) discloses a moving body tracing irradiation device capable of automatically calculating, in actual time, position of tumor moving around in the trunk and capable ensuring the actually required accuracy without depending on the absolute accuracy of a mechanical system. This moving body tracing irradiation device is characterized by being provided with: a linac which irradiates tumor with therapeutic beams; a tumor marker which is embedded near the tumor; a first x-ray fluoroscope which images the tumor marker from a first direction; a second x-ray fluoroscope which images the tumor marker from a second direction simultaneously with the first x-ray fluoroscope; a first and a second image input parts which digitize a first and a second fluoroscopic images outputted from the first and second x-ray fluoroscopes; a first and a second recognition processing parts which execute, at an actual time level of a predetermined frame rate, template matching by a gray scale normalization cross-correlation method in which a template image of a tumor marker previously registered is effected on image information digitized by the first and second image input parts to thereby obtain first and second two-dimensional coordinates of the tumor marker; a central processing part which calculates three-dimensional coordinates of the tumor marker from the first and second two-dimensional coordinates calculated by the first and second recognition processing parts; and an irradiation control part which controls the therapeutic beams of the linac based on the obtained three-dimensional coordinates of the tumor marker.

Japanese Patent JP3432268B discloses a radiotherapy system capable of resolving deterioration in accuracy in irradiation planning due to body movement of a subject during radiotherapy. The radiotherapy system is characterized by being provided with: in radiotherapy system performing radiotherapy by irradiating a subject with radiation, phase identification means adapted to establish association between the phase of living body data in accordance with the body movement of the subject detected in parallel with acquisition of a CT image of the subject and the phase of the CT image; plan data creation means adapted to, based on the CT image associated with the phase of the living body data by the phase identification means, create treatment plan data including opening and closing data of a collimator for adjusting a field to be irradiated with the radiation; determination means adapted to determine correlation between the living body data associated with the phase of the CT image and the living body data in accordance with the body movement of the subject obtained during the radiotherapy; and collimator control means adapted to, in accordance with a result of determination made by the determination means, perform opening and closing control of the collimator based on the opening and closing data.

Japanese Patent JP3326597B discloses a respiration synchronizing control device. This control device is characterized by the use of function of a semiconductor position detecting element (PSD) and composed of: a light source part with a light source position or a light direction fluctuating in correspondence with the fluctuation of the outer skin of an organism interlocked with respiration; the PSD receiving light from the light source part, as a fluctuation signal of the outer skin of the organism and converting it into an electric signal corresponding to the cycle phase of respiration; and a control circuit sending an actuation control signal of other controlled equipment on the basis of this electric signal.

Japanese Laid Open Patent Application JP H4-507048A (corresponding to WO9011721) discloses a patient alignment system and procedure for radiation treatment. In this patent, accurate and repeatable patient alignment with a charged-particle beam of a radiation beam therapy system, such as a proton beam delivery system, is provided. The patient is immobilized within a formfit patient pod. Reference radiographs are prepared with an X-ray system that is used for repositioning the patient within the pod on subsequent occasions. CT scan data is obtained using a CT Scan System of a particular tissue volume of interest, such as a region of the patient wherein a cancerous tumor is located, while the patient remains in the pod. The CT scan data is used to prepare a treatment plan for the patient. The treatment plan includes identifying an isocenter within the tissue volume at which the beam is to be directed from a selected angle(s). A computer simulation of the treatment plan is performed to optimize the treatment plan.

Japanese Patent JP3394250B (corresponding to WO92006644) discloses an apparatus for and method of stereotaxic surgery. The method and the apparatus are set forth for selectively irradiating a target within a patient. A 3-dimensional mapping is provided of a mapping region surrounding the target. A beaming apparatus emits a collimated beam. Diagnostic beams at a known non-zero angle to one another pass through the mapping region. They produce images of projections within the mapping region. Electronic representations of the images are compared with the reference data thereby locating the target. The relative positions of the beaming apparatus and the living organism are adjusted in such a manner that the collimated beam is focused on the target region. The comparison is repeated at small time intervals and, when the comparison so indicates, the adjusting step is repeated, as needed, and in such a manner that the collimated beam remains focused onto the target region.

Japanese Laid Open Patent Application JP H8-511452A (corresponding to WO9428971) discloses a radiotherapy system. The radiation therapy machine having constrained angular freedom to produce a beam only within a gantry plane. A radiation shield may be stationary and not attached to the gantry or rotating to always block the primary beam. The constrained motion reduces the risk of patient/gantry collision and provides for extremely accurate radiation therapy planning. The therapy machine, so constrained, may include a tomographic imaging system on a single gantry. The two systems cooperate and employ many of the same hardware components to both plan and carry out therapy sessions in which irregularly shaped treatment volumes are accurately irradiated while tissue surrounding those volumes is minimally irradiated. The therapy machine also may include a collimator that changes the width of a fan beam of radiation as a treatment volume of the patient crosses the volume exposed by the beam so as to minimize the irradiation of healthy tissue at the front and back of the tumor. The width of the fan beam may be controlled to treat multiple adjacent, similar slices of the patient at one time reducing the treatment duration.

SUMMARY OF THE INVENTION

It is an object of the present invention to provide a radiotherapy device control apparatus and a radiation irradiation method which can match predetermined position of a subject with predetermined position of a radiotherapy device with a higher accuracy.

It is another object of the present invention to provide a radiotherapy device control apparatus and a radiation irradiation method which can facilitate user operation of matching predetermined position of a subject with the predetermined position of the radiotherapy device.

It is still another object of the present invention to provide a radiotherapy device control apparatus and a radiation irradiation method which can reduce the burden imposed on a subject upon matching predetermined position of the subject with the predetermined position of the radiotherapy device with the higher accuracy.

It is still another object of the present invention to provide a radiotherapy device control apparatus and a radiation irradiation method which can match the predetermined three-dimensional position of a subject with the predetermined three-dimensional position of the radiotherapy device with the higher accuracy.

It is still another object of the present invention to provide a radiotherapy device control apparatus and a radiation irradiation method which can reduce costs involved in matching the predetermined position of a subject with the predetermined position of the radiotherapy device with the higher accuracy.

It is still another object of the present invention to provide a radiotherapy device control apparatus and a radiation irradiation method which can reduce costs involved in constructing a system for matching the predetermined position of a subject with the predetermined position of the radiotherapy device with the higher accuracy.

It is still another object of the present invention to provide a radiotherapy device control apparatus and a radiation irradiation method which can achieve saving of space for arranging the system for matching the predetermined position of a subject with the predetermined position of the radiotherapy device with the higher accuracy.

This and other objects, features and advantages of the present invention will be readily ascertained by referring to the following description and drawings.

In order to achieve an aspect of the present invention, the present invention provides a radiotherapy device control apparatus including: a reference image creation section; a transmitted image creation section; and an affected area position control section, wherein the radiotherapy device control apparatus controls a radiotherapy device. The radiotherapy device includes: a therapeutic radiation irradiation device which radiates therapeutic radiation, an imager which generates an imager image of a subject by using radiation transmitted through the subject, and a drive device which moves a couch, on which the subject is arranged, with respect to the therapeutic radiation irradiation device. The reference image creation section collects a reference imager image taken by the imager. The transmitted image creation section takes a transmitted imager image of the subject by the imager. The affected area position control section judge whether or not a relative position of the couch with respect to the therapeutic radiation irradiation device is appropriate based on a first position at which a characteristic point of the subject is displayed in the transmitted imager image and a second position at which the characteristic point is displayed in the reference imager image. The affected area position control section may change the relative position of the couch by using the drive device based on the first position and the second position.

In the radiotherapy device control apparatus, the imager may take the reference imager image when a part of the subject is arranged to be irradiated with the therapeutic radiation. The affected area position control section, when a first relative position coincide with a second relative position, may change the relative position of the couch by using the drive device such that the first position coincides with the second position, the first relative position is a relative position of the imager with respect to the therapeutic radiation irradiation device when the transmitted imager image is taken, and the second relative position is a relative position of the imager with respect to the therapeutic radiation irradiation device when the reference imager image is taken.

In the radiotherapy device control apparatus, the affected area position control section, based on a relation between the second position and a third position of a part of the subject, may change the relative position of the couch by using the drive device such that the third position calculated by using the first position is irradiated with the therapeutic radiation.

In the radiotherapy device control apparatus, the drive device may include: a couch drive device which moves the couch, and a irradiation drive device which moves the therapeutic radiation irradiation device. The affected area position control section may change the relative position of the couch by preferentially using the irradiation drive device.

In the radiotherapy device control apparatus, the imager may include: a first imager, and a second imager. The reference imager image may include: a first reference imager image which is taken by the first imager, and a second reference imager image which is taken by the second imager. The transmitted imager image may include: a first transmitted imager image which is taken by the first imager, and a second transmitted imager image which is taken by the second imager. The affected area position control section may change the relative position of the couch by using the drive device based on a third position at which a characteristic point of the subject is displayed in the first transmitted imager image, a fourth position at which the characteristic point is displayed in the first reference imager image, a fifth position at which a characteristic point of the subject is displayed in the second transmitted imager image, and a sixth position at which the characteristic point is displayed in the second reference imager image.

In the radiotherapy device control apparatus, the imager may include: a radiation imager which generates at least one of the transmitted imager image and the reference imager image by using the therapeutic radiation.

The radiotherapy device control apparatus may further include: a three-dimensional data creation section which creates a three-dimensional data of the subject based on a transmitted image taken by the imager; and a two-dimensional image creation section which creates a two-dimensional image based on the three-dimensional data. The affected area position control section may change the relative position of the couch by using the drive device based on the first position and a position at which the characteristic point is displayed in the two-dimensional image.

The radiotherapy device control apparatus may further include: a three-dimensional data collection section which collects a three-dimensional data of the subject, the three-dimensional data is created by a three-dimensional imaging device provided in addition to the radiotherapy device; and a two-dimensional image creation section which creates a two-dimensional image based on the three-dimensional data. The affected area position control section may change the relative position of the couch by using the drive device based on the first position and a position at which the characteristic point is displayed in the two-dimensional image.

In order to achieve another aspect of the present invention, the present invention provides a radiotherapy system including: a radiotherapy device control apparatus according to any of the above-mentioned radiotherapy device control apparatuses; and a radiotherapy device.

In order to achieve another aspect of the present invention, the present invention provides a radiation irradiation method using a radiotherapy device. The radiotherapy device includes: a therapeutic radiation irradiation device which radiates therapeutic radiation, an imager which generates an imager image of a subject by using radiation transmitted through the subject, and a drive device which moves a couch, on which the subject is arranged, with respect to the therapeutic radiation irradiation device. The radiation irradiation method include: (a) collecting a reference imager image taken by the imager, (b) imaging a transmitted imager image of the subject by the imager, (c) judging whether or not a relative position of the couch with respect to the therapeutic radiation irradiation device is appropriate based on a first position at which a characteristic point of the subject is displayed in the transmitted imager image and a second position at which the characteristic point is displayed in the reference imager image, and (d) changing the relative position of the couch by using the drive device based on the first position and the second position.

In the radiation irradiation method, the reference imager image may be taken by the imager when a part of the subject is arranged to be irradiated with the therapeutic radiation. The relative position of the couch may be changed by using the drive device when a first relative position coincide with a second relative position such that the first position coincides with the second position, the first relative position is a relative position of the imager with respect to the therapeutic radiation irradiation device when the transmitted imager image is taken, and the second relative position is a relative position of the imager with respect to the therapeutic radiation irradiation device when the reference imager image is taken.

In the radiation irradiation method, the relative position of the couch may be changed by using the drive device based on a relation between the second position and a third position of a part of the subject such that the third position calculated by using the first position is irradiated with the therapeutic radiation.

In the radiation irradiation method, the drive device may include: a couch drive device which moves the couch, and a irradiation drive device which moves the therapeutic radiation irradiation device. The irradiation drive device may be used in preference to the couch drive device when the relative position of the couch is changed.

In the radiation irradiation method, the imager may include: a first imager, and a second imager. The reference imager image may include: a first reference imager image which is taken by the first imager, and a second reference imager image which is taken by the second imager. The transmitted imager image may include: a first transmitted imager image which is taken by the first imager, and a second transmitted imager image which is taken by the second imager. The method may further include: (e) changing the relative position of the couch by using the drive device based on a third position at which a characteristic point of the subject is displayed in the first transmitted imager image, a fourth position at which the characteristic point is displayed in the first reference imager image, a fifth position at which a characteristic point of the subject is displayed in the second transmitted imager image, and a sixth position at which the characteristic point is displayed in the second reference imager image.

In the radiation irradiation method, the imager may include: a radiation imager which generates at least one of the transmitted imager image and the reference imager image by using the therapeutic radiation.

The radiation irradiation method may further include: (f) creating a three-dimensional data of the subject based on a transmitted image taken by the imager, and (g) creating a two-dimensional image based on the three-dimensional data, (h) changing the relative position of the couch by using the drive device based on the first position and a position at which the characteristic point is displayed in the two-dimensional image.

In the radiation irradiation method may further include: (i) collecting a three-dimensional data of the subject, the three-dimensional data is created by a three-dimensional imaging device provided in addition to the radiotherapy device, (j)

creating a two-dimensional image based on the three-dimensional data, and (k) changing the relative position of the couch by using the drive device based on the first position and a position at which the characteristic point is displayed in the two-dimensional image.

In order to achieve another aspect of the present invention, the present invention provides computer program product with program code means for carrying out all steps according to any of the above-mentioned radiation irradiation methods if the program runs on a computer.

The present invention provides computer program product with program code means according to the above-mentioned computer program product which are stored on a storage means which can be read by the computer.

A radiotherapy device control apparatus and a radiation irradiation method according to the present invention can match position where therapeutic radiation is irradiated with predetermined position of a subject with the higher accuracy.

The radiotherapy device control apparatus and the radiation irradiation method according to the present invention can facilitate user operation of matching predetermined position of a subject with the predetermined position of the radiotherapy device.

The radiotherapy device control apparatus and the radiation irradiation method according to the present invention can reduce the burden imposed on a subject upon matching predetermined position of the subject with predetermined position of the radiotherapy device with the higher accuracy.

The radiotherapy device control apparatus and the radiation irradiation method according to the present invention can match a predetermined three-dimensional position of a subject with a predetermined three-dimensional position of the radiotherapy device with the higher accuracy.

The radiotherapy device control apparatus and the radiation irradiation method according to the present invention can reduce costs involved in matching predetermined position of a subject with the predetermined position of the radiotherapy device with the higher accuracy.

The radiotherapy device control apparatus and the radiation irradiation method according to the present invention can reduce cost involved in constructing a system for matching predetermined position of a subject with the predetermined position of the radiotherapy device with the higher accuracy.

The radiotherapy device control apparatus and the radiation irradiation method according to the present invention can achieve saving of space for arranging the system for matching predetermined position of a subject with the predetermined position of the radiotherapy device with the higher accuracy.

DESCRIPTION OF THE PREFERRED EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposed.

Embodiments of a radiotherapy system according to the present invention will be described below referring to the accompanying drawings.

Figure 1:
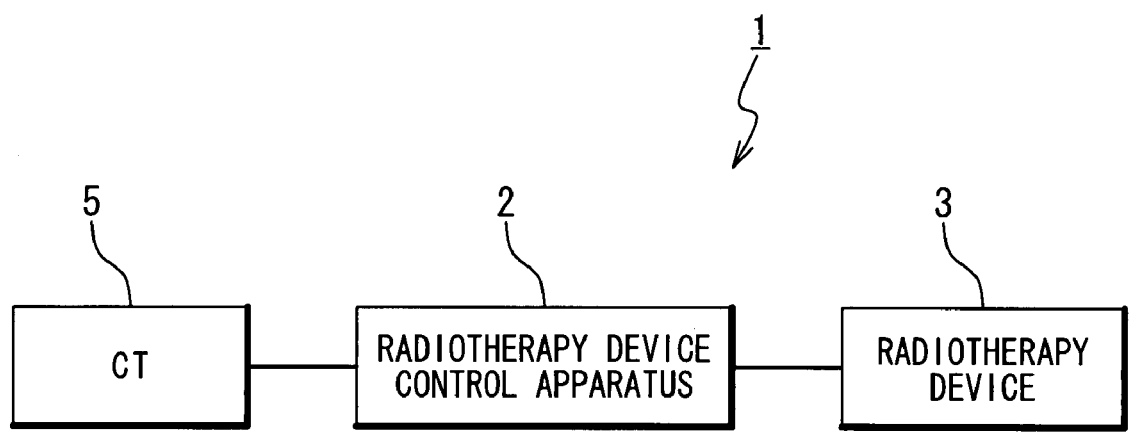
FIG. 1 is a block diagram showing a radiotherapy system in the embodiment.

FIG. 1 is a block diagram showing a radiotherapy system 1 in the embodiment. The radiotherapy system 1 is provided with a radiotherapy device control apparatus 2, a radiotherapy device 3, and a CT (computerized tomographic apparatus) 5. The radiotherapy device control apparatus 2 is a computer exemplified by a personal computer. The radiotherapy device control apparatus 2 is connected to the radiotherapy device 3 and the CT 5 so as to be capable of transmitting information bi-directionally.

The CT 5 photographs (takes) a plurality of transmitted images by transmitting X-rays through a human body from various directions, and then subjects the plurality of transmitted images to image processing by a computer to thereby generate images of cross sections of the human body and also subjects the plurality of transmitted images to image processing by the computer to thereby generate three-dimensional data indicating inner condition of the human body. The CT 5 can be replaced with a different device, for example, an MRI device, which measures three-dimensional condition of the human body. The MRI device detects magnetism possessed by cells in the human body by using nuclear magnetic resonance and then transforms this magnetism into an image by a computer to thereby generate three-dimensional data indicating inner condition of the human body.

Figure 2:
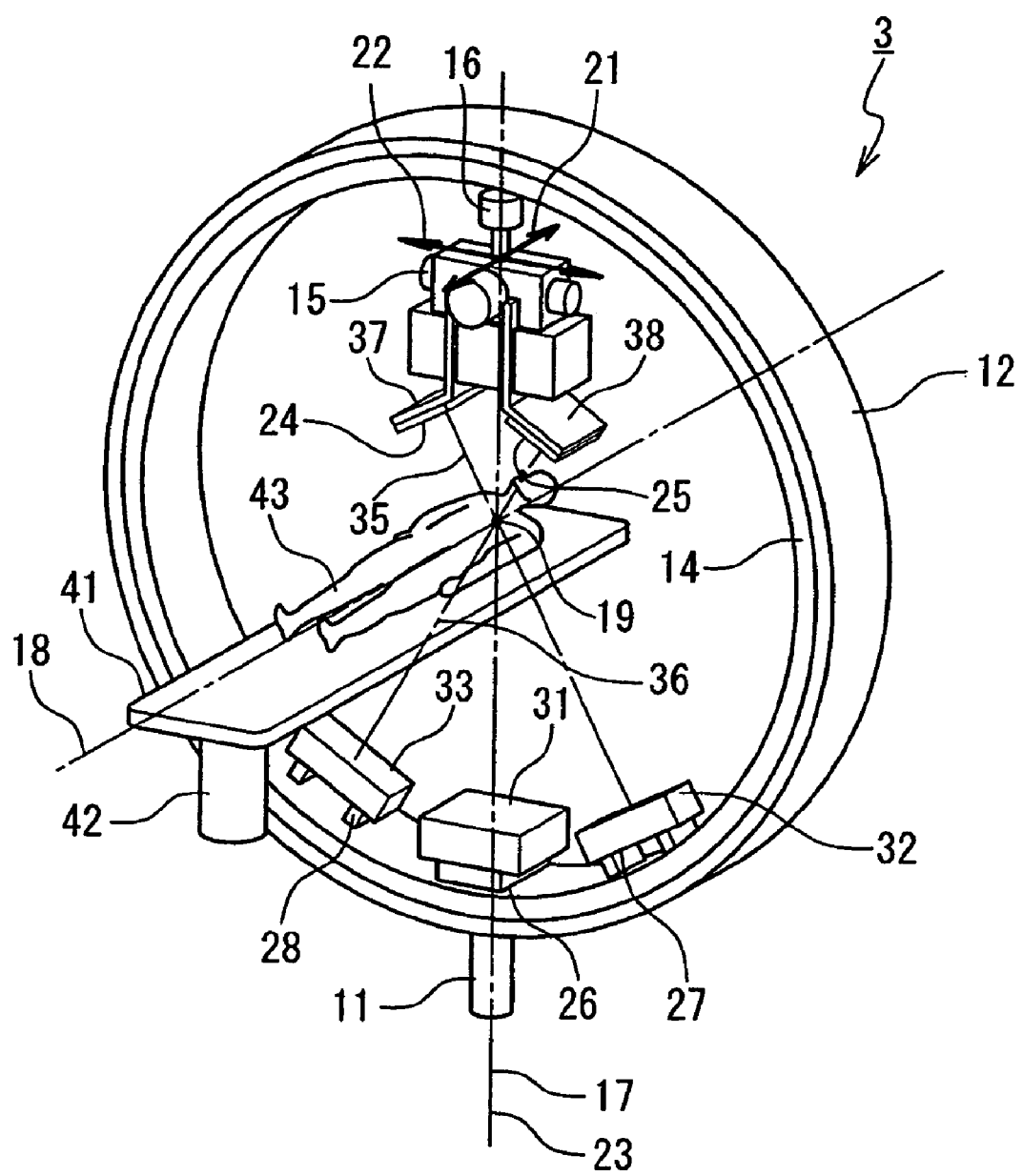
FIG. 2 is a perspective view showing a radiotherapy device of the radiotherapy system.

FIG. 2 is a perspective view showing the radiotherapy device 3 of the radiotherapy system 1 in the embodiment. The radiotherapy device 3 is provided with a turning drive device 11, an O ring 12, a travel gantry 14, a head swing device 15, and a therapeutic radiation irradiation device 16. The turning drive device 11 supports the O ring 12 to a base so that the O ring 12 is rotatable around a rotation axis 17, and is controlled by the radiotherapy device control apparatus 2 to rotate the O ring 12 around the rotation axis 17. The rotation axis 17 is parallel with the vertical direction. The O ring 12 is formed into a ring shape with a rotation axis 18 serving as a center, and supports the travel gantry 14 so that the travel gantry 14 is rotatable around the rotation axis 18. The rotation axis 18 is perpendicular to the vertical direction, and passes through an isocenter 19 included in the rotation axis 17. The rotation axis 18 is further fixed with respect to the O ring 12, that is, the O ring 12 rotates the travel gantry 14 around the rotation axis 18, and the O ring 12 rotates around the rotation axis 18. The travel gantry 14 is formed into a ring shape with the rotation axis 18 serving as a center, and so arranged as to be concentric with the ring of the O ring 12. The radiotherapy device 3 is further provided with a traveling drive device, which is not shown. The traveling drive device (not shown) is controlled by the radiotherapy device control apparatus 2 to rotate the travel gantry 14 around the rotation axis 18.

The head swing device 15 is fixed inside the ring of the travel gantry 14 to support the therapeutic radiation irradiation device 16 to the travel gantry 14. The head swing device 15 has a pan axis 21 and a tilt axis 22. The pan axis 21 is fixed with respect to the travel gantry 14 and is parallel to the rotation axis 18 without intersecting therewith. The tilt axis 22 is fixed with respect to the travel gantry 14 and orthogonal to the pan axis 21. The head swing device 15 is controlled by the radiotherapy device control apparatus 2 to rotate the therapeutic radiation irradiation device 16 around the pan axis 21 and also rotates the therapeutic radiation irradiation device 16 around the tilt axis 22. The therapeutic radiation irradiation device 16 is controlled by the radiotherapy device control apparatus 2 to radiate therapeutic radiation 23.

Once the therapeutic radiation irradiation device 16 is supported by the travel gantry 14 as described above and is adjusted by the head swing device 15 so as to be directed toward the isocenter 19, the therapeutic radiation 23 always passes approximately through the isocenter 19 even when the O ring 12 is rotated by the turning drive device 11 or when the travel gantry 14 is rotated by the traveling drive device.

The radiotherapy device 3 is further provided with a plurality of imager systems. Specifically, the radiotherapy device 3 is provided with radiation source drive devices 37 and 38, diagnostic X-ray sources 24 and 25, sensor array drive devices 27 and 28, and sensor arrays 32 and 33. The radiation source drive device 37 is fixed inside the ring of the travel gantry 14, supports the diagnostic X-ray source 24 to the travel gantry 14, and is controlled by the radiotherapy device control apparatus 2 to move the diagnostic X-ray source 24 with respect to the travel gantry 14. The diagnostic X-ray source 24 is arranged inside the ring of the travel gantry 14 and at position such that a line segment linking from the isocenter 19 to the diagnostic X-ray source 24 and a line segment linking from the isocenter 19 to the therapeutic radiation irradiation device 16 forms an acute angle. The diagnostic X-ray source 24 is controlled by the radiotherapy device control apparatus 2 to radiate diagnostic X-rays 35 toward the isocenter 19. The diagnostic X-rays 35 are radiated from one point included in the diagnostic X-ray source 24, and are cone beams of a conical shape with the aforementioned point serving as a vertex. The radiation source drive device 38 is fixed inside the ring of the travel gantry 14, supports the diagnostic X-ray source 25 to the travel gantry 14, and is controlled by the radiotherapy device control apparatus 2 to move the diagnostic X-ray source 24 with respect to the travel gantry 14. The diagnostic X-ray source 25 is arranged inside the ring of the travel gantry 14 and at position such that a line segment linking from the isocenter 19 to the diagnostic X-ray source 25 and a line segment linking from the isocenter 19 to the therapeutic radiation irradiation device 16 forms an acute angle. The diagnostic X-ray source 25 is controlled by the radiotherapy device control apparatus 2 to radiate diagnostic X-rays 36 toward the isocenter 19. The diagnostic X-rays 36 are radiated from one point included in the diagnostic X-ray source 25, and are cone beams of a conical shape with the aforementioned point serving as a vertex.

The sensor array drive device 27 is fixed inside the ring of the travel gantry 14, supports the sensor array 32 to the travel gantry 14, and is controlled by the radiotherapy device control apparatus 2 to move the sensor array 32 with respect to the travel gantry 14. The sensor array drive device 28 is fixed inside the ring of the travel gantry 14, supports the sensor array 33 to the travel gantry 14, and is controlled by the radiotherapy device control apparatus 2 to move the sensor array 33 with respect to the travel gantry 14. The sensor array 32 receives the diagnostic X-rays 35 radiated by the diagnostic X-ray source 24 and transmitted through a subject around the isocenter 19 to generate a transmitted image of the subject. The sensor array 33 receives the diagnostic X-rays 36 radiated by the diagnostic X-ray source 25 and transmitted through the subject around the isocenter 19 to generate a transmitted image of the subject. The sensor arrays 32 and 33 are exemplified by FPDs (Flat Panel Detectors) and X-rays II (Image Intensifiers).

According to such imager systems, even when the diagnostic X-ray sources 24 and 25 are moved by the radiation source drive devices 37 and 38, the sensor arrays 32 and 33 can be appropriately moved by the sensor array drive devices 27 and 28, respectively, thus generating transmitted images with the isocenter 19 serving as a center thereof.

The radiotherapy device 3 is further provided with a sensor array drive device 26 and a sensor array 31. The sensor array drive device 26 is fixed inside the ring of the travel gantry 14, supports the sensor array 31 to the travel gantry 14, and is controlled by the radiotherapy device control apparatus 2 to move the sensor array 31 with respect to the travel gantry 14. The sensor array 31 receives the therapeutic radiation 23 radiated by the therapeutic radiation irradiation device 16 and transmitted through a subject around the isocenter 19 to generate a transmitted image of the subject. The sensor array 31 is exemplified by an FPD (Flat Panel Detector) and X-rays II (Image Intensifier). In this case, even when the therapeutic radiation irradiation device 16 is moved by the head swing device 15, the sensor array 31 can be appropriately moved by the sensor array drive device 26, thus generating a transmitted image with the isocenter 19 serving as a center thereof.

The diagnostic X-ray source 24 can also be arranged at a position such that a line segment linking from the isocenter 19 to the diagnostic X-ray source 24 and a line segment linking from the isocenter 19 to the therapeutic radiation irradiation device 16 forms an obtuse angle. That is, the sensor array 32 is arranged at position such that a line segment linking from the isocenter 19 to the sensor array 32 and a line segment linking from the isocenter 19 to the therapeutic radiation irradiation device 16 forms an acute angle. The diagnostic X-ray source 25 can also be arranged at position such that a line segment linking from the isocenter 19 to the diagnostic X-ray source 25 and a line segment linking from the isocenter 19 to the therapeutic radiation irradiation device 16 forms an obtuse angle. That is, the sensor array 33 is arranged at position such that a line segment linking from the isocenter 19 to the sensor array 33 and a line segment linking from the isocenter 19 to the therapeutic radiation irradiation device 16 forms an acute angle. In this case, the sensor arrays 32 and 33 are less likely to be irradiated with the therapeutic radiation 23 radiated from the therapeutic radiation irradiation device 16, which is preferable.

The radiation source drive devices 37 and 38 can also support the diagnostic X-ray sources 24 and 25, respectively, to the therapeutic radiation irradiation device 16. In this case, even when the therapeutic radiation irradiation device 16 is moved by the head swing device 15, the relative position of the radiotherapy device 3 with respect to the therapeutic radiation irradiation device 16 is fixed, so that the radiotherapy device 3 can more easily control the position of the diagnostic X-ray sources 24 and 25, which is preferable.

The radiotherapy device 3 is further provided with a couch (table) 41 and a couch (table) drive device 42. The couch 41 is used for laying a patient 43 to be treated by the radiotherapy system 1. The couch 41 is provided with a fixing tool (not shown). This fixing tool fixes the patient to the couch 41 so that he or she does not move. The couch drive device 42 supports the couch 41 to the base and is controlled by the radiotherapy device control apparatus 2 to move the couch 41.

Figure 3:
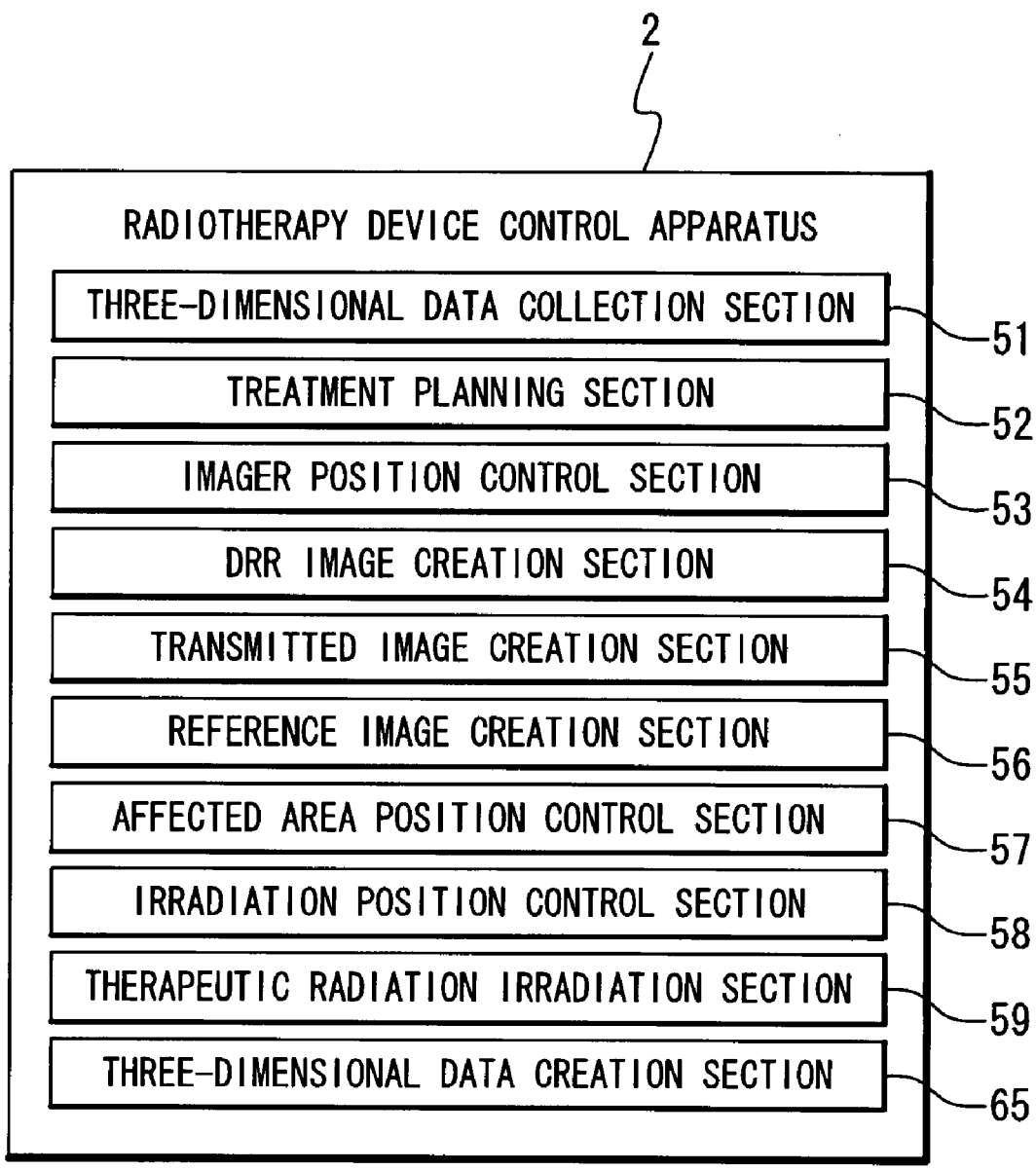
FIG. 3 is a block diagram showing a radiotherapy device control apparatus of the radiotherapy system in the embodiment.

FIG. 3 is a block diagram showing the radiotherapy device control apparatus 2 of the radiotherapy system 1 in the embodiment. The radiotherapy device control apparatus 2 is a computer, and is provided with a CPU, a storage device, an input device, an output device, and an interface (all not shown). The CPU executes a computer program installed in the radiotherapy device control apparatus 2 to control the storage device, the input device, and the output device thereof. The storage device stores the computer program, information used by the CPU, and information generated by the CPU. The input device supplies to the CPU information generated through user's operation. The input device is exemplified by a keyboard and a mouse. The output device outputs information generated by the CPU in a manner such that the information can be recognized by the user. The output device is exemplified by a display. The interface outputs to the CPU information generated by an external device connected to the radiotherapy device control apparatus 2 and outputs to the external device information generated by the CPU.

The radiotherapy device control apparatus 2 is provided with: as computer programs, a three-dimensional data collection section 51, a treatment planning section 52, an imager position control section 53, a DRR image creation section 54, a transmitted image creation section 55, a reference image creation section 56, an affected area position control section 57, an irradiation position control section 58, and a therapeutic radiation irradiation section 59. Here, a three-dimensional data creation section 65 may be included in the radiotherapy device control apparatus 2.

The three-dimensional data collection section 51 collects from the CT 5 three-dimensional data generated by the CT 5 and indicating positional relationship between an affected area of the patient 43 and the organs around the affected area, and stores the three-dimensional data in the storage device in association with identification information of the patient 43. The three-dimensional data collection section 51 can also collect from the CT 5 a plurality of transmitted images photographed (taken) by transmitting X-rays through the patient 43 from various directions, can subject the plurality of transmitted images to image processing by a computer to thereby generate images of cross sections of the patient 43, and can subject the plurality of transmitted images to image processing by the computer to thereby generate three-dimensional data indicating inner condition of the patient 43.

The treatment planning section 52, based on the three-dimensional data collected by the three-dimensional data collection section 51 and information inputted by a user, creates a treatment plan, and stores the treatment plan in the storage device in association with the identification information of the patient 43. The treatment plan indicates irradiation angles at which the affected area of the patient 43 is irradiated with the therapeutic radiation 23 and the dosage and property of the therapeutic radiation 23 irradiated from each of the irradiation angles. The treatment plan further indicates imaging angles at which the diagnostic X-rays 35 and 36 are irradiated such that transmitted images taken by transmission of the diagnostic X-rays 35 and 36 through the patient 43 displays the affected area of the patient 43 more precisely when the therapeutic radiation 23 is irradiated from various irradiation angles. The imaging angles do not have to be indicated by the treatment plan, and can be inputted to the radiotherapy device control apparatus 2 separately from the treatment plan.

The imager position control section 53 controls the radiation source drive device 37 to move the diagnostic X-ray source 24 so that the diagnostic X-rays 35 are irradiated to the patient 43 at the imaging angle indicated by the treatment plan created by the treatment planning section 52, and controls the sensor array drive device 27 to move the sensor array 32 so that the transmitted image obtained by the diagnostic X-rays 35 mainly displays the affected area of the patient 43 in the center. The imager position control section 53 further controls the radiation source drive device 38 to move the diagnostic X-ray source 25 so that the diagnostic X-rays 36 are irradiated to the patient 43 at the imaging angle indicated by the treatment plan, and controls the sensor array drive device 28 to move the sensor array 33 so that the transmitted image obtained by the diagnostic X-rays 36 mainly displays the affected area of the patient 43 in the center. The imager position control section 53 further controls the radiation source drive device 38 to move the diagnostic X-ray source 25 so that the diagnostic X-rays 36 are irradiated to the patient 43 at the imaging angle, and controls the sensor array drive device 28 to move the sensor array 33 so that the transmitted image obtained by the diagnostic X-rays 36 mainly displays the affected area of the patient 43 in the center. The imager position control section 53 further controls the head swing device 15 to move the therapeutic radiation irradiation device 16 so that the therapeutic radiation 23 is irradiated to the patient 43 at the imaging angle indicated by the treatment plan, and controls the sensor array drive device 26 to move the sensor array 31 so that the transmitted image obtained by the therapeutic radiation 23 mainly displays the affected area of the patient 43 in the center.

The DRR image creation section 54, based on the three-dimensional data collected by the three-dimensional data collection section 51, calculates a DRR image, and stores the DRR image in the storage device in association with the identification information of the patient 43. The DRR image indicates a two-dimensional image which is taken when X-rays are transmitted at the imaging angle indicated by the treatment plan created by the treatment planning section 52. The DRR image creation section 54, based on information inputted by the user, further adds a mark to the position in the DRR image where a characteristic point of the patient 43 is displayed.

The transmitted image creation section 55 radiates the diagnostic X-rays 35 by using the diagnostic X-ray source 24 and takes a transmitted image of the patient 43 generated by using the sensor array 32 based on the diagnostic X-rays 35. The transmitted image creation section 55 further radiates the diagnostic X-rays 36 by using the diagnostic X-ray source 25 and takes a transmitted image of the patient 43 generated by using the sensor array 33 based on the diagnostic X-rays 36. The transmitted image creation section 55 further stores the transmitted images in the storage device in association with the identification information of the patient 43. With the plurality of transmitted images taken in this manner, three-dimensional position of the characteristic point of the patient 43 can be calculated. The characteristic point is exemplified by a portion (bone or the like) of internal organs of the patient 43 which is easy to appear in the transmitted image and a gold mark embedded in a portion thereof which moves in conjunction with the affected area of the patient 43. Further, the transmitted image creation section 55 can also radiate the therapeutic radiation 23 by using the therapeutic radiation irradiation device 16 and take a transmitted image of the patient 43 generated by using the sensor array 31 based on the therapeutic radiation 23. Further using the transmitted image obtained by the therapeutic radiation 23 permits calculating the three-dimensional position of the characteristic point of the patient 43 with higher accuracy. The transmitted image creation section 55 can also take only the transmitted image obtained by X-rays of one of the diagnostic X-rays 35 and 36 and the transmitted image obtained by the therapeutic radiation rays 23. Also in this case, the three-dimensional position of the characteristic point of the patient 43 can be calculated by using these two transmitted images. The transmitted image creation section 55 can also take only the transmitted image obtained by X-rays of one of the diagnostic X-rays 35 and 36 and the therapeutic radiation 23. In this case, the three-dimensional position of the characteristic point of the patient 43 cannot be calculated.

The reference image creation section 56 collects the transmitted images taken by the transmitted image creation section 55 from the storage device, and creates a reference image on the basis of the transmitted images. The transmitted images serving as a basis for creating the reference image is taken in the past before treatment operation executed by using this reference image, for example, a transmitted image taken by the transmitted image creation section 55 when the affected area of the patient 43 is so arranged as to be irradiated with the therapeutic radiation 23 in previous treatment operation. The reference image creation section 56, based on information inputted by the user, further adds a mark to position in the reference image where the characteristic point of the patient 43 is projected.

The affected area position control section 57 compares the transmitted image taken by the transmitted image creation section 55 with the DRR image generated by the DRR image creation section 54 to judge whether or not the affected area of the patient 43 is to be irradiated with the therapeutic radiation 23. The affected area position control section 57 further compares the transmitted image taken by the transmitted image creation section 55 with the DRR image generated by the DRR image creation section 54 to calculate such couch position of the couch 41 that permits the affected area of the patient 43 to be irradiated with the therapeutic radiation 23. For example, the couch position is position of the couch 41 when the affected area of the patient 43 is arranged at the isocenter 19. The couch position can be calculated based on the position of the mark added to the DRR image and the position of the characteristic point displayed in the transmitted image. The affected area position control section 57 moves the patient 43 by moving the couch 41 to the calculated position by using the couch drive device 42. That is, the affected area position control section 57 moves the patient 43 by using the couch drive device 42 so that the affected area of the patient 43 is irradiated with the therapeutic radiation 23. For example, the affected area position control section 57 moves the patient 43 by using the couch drive device 42 so that the transmitted image taken by the transmitted image creation section 55 matches with the DRR image generated by the DRR image creation section 54. For example, the affected area position control section 57 calculates a difference between the position of the characteristic point displayed in the transmitted image and the position of the characteristic point displayed in the DRR image. For example, the difference indicates the direction of the characteristic point of the DRR image with respect to the characteristic point of the transmitted image and the distance between the two characteristic points when the transmitted image and the DRR image are superimposed one on another. The affected area position control section 57, based on the difference, calculates the direction and distance in and by which the patient 43 is to be moved, and moves the couch 41 based on the direction and the distance.

The affected area position control section 57 further compares the transmitted image taken by the transmitted image creation section 55 with the reference image taken by the reference image creation section 56 to calculate such couch position of the couch 41 that permits the affected area of the patient 43 to be irradiated with the therapeutic radiation 23. The couch position can be calculated based on the position of the mark added to the reference image and the position of the characteristic point displayed in the transmitted image. For example, the affected area of the patient 43 is irradiated with the therapeutic radiation 23 if the relative position of the imager system with respect to the therapeutic radiation irradiation device 16 when the reference image is taken and the relative position of the imager system with respect to the therapeutic radiation irradiation device 16 when the transmitted image is taken match with each other and also if the position of the characteristic point in the transmitted image and the position of the characteristic point in the reference image match with each other. The affected area position control section 57 moves the patient 43 by moving the couch 41 to the calculated position by using the couch drive device 42. That is, the affected area position control section 57 moves the couch 41 so that the affected area of the patient 43 is irradiated with the therapeutic radiation 23. For example, if the position of the imager system with respect to the therapeutic radiation irradiation device 16 when the reference image is taken and the position of the imager system with respect to the therapeutic radiation irradiation device 16 when the transmitted image is taken match with each other, the affected area position control section 57 moves the patient 43 by using the couch drive device 42 so that the transmitted image taken by the transmitted image creation section 55 matches with the reference image generated by the reference image creation section 56. For example, the affected area position control section 57 calculates a difference between the position of the characteristic point displayed in the transmitted image and the position of the characteristic point displayed in the reference image. For example, the difference indicates the direction of the characteristic point of the reference image with respect to the characteristic point of the transmitted image and the distance between the two characteristic points when the transmitted image and the reference image are superimposed one on another. The affected area position control section 57, based on the difference, calculates the direction and distance in and by which the patient 43 is to be moved, and moves the couch 41 based on the direction and the distance.

The affected area position control section 57 can also move the patient 43 by using the couch drive device 42 based on information inputted by the user. In this case, the affected area position control section 57 displays on the display the transmitted image taken by the transmitted image creation section 55 and the DRR image generated by the DRR image creation section 54. The user compares the transmitted image with the DRR image, and inputs to the radiotherapy device control apparatus 2 the direction and distance in and by which the patient 43 is moved. The affected area position control section 57 moves the patient 43 by using the couch drive device 42 based on the inputted information. Further, the affected area position control section 57 displays on the display the transmitted image taken by the transmitted image creation section 55 and the reference image generated by the reference image creation section 56. The user compares the transmitted image with the reference image, and inputs to the radiotherapy device control apparatus 2 the direction and distance in and by which the patient 43 is moved. The affected area position control section 57 moves the patient 43 by using the couch drive device 42 based on the inputted information.

The affected area position control section 57 can also control the relative position of the patient 43 with respect to the therapeutic radiation 23 by further using the turning drive device 11 or the traveling drive device for rotating the travel gantry 14 around the rotation axis 18 or the head swing device 15. In this case, the affected area position control section 57 uses the turning drive device 11 or the traveling drive device or the head swing device 15 preferentially prior to the couch drive device 42. Such movement can reduce the load of moving the patient 43, which is preferable.

The irradiation position control section 58 calculates three-dimensional position of the affected area based on the position of the affected area displayed in the transmitted image taken by the transmitted image creation section 55, and moves the therapeutic radiation irradiation device 16 by using the head swing device 15 so that the therapeutic radiation 23 is transmitted through the three-dimensional position. The irradiation position control section 58 can also move the therapeutic radiation irradiation device 16 by further using the turning drive device 11 or the traveling drive device for rotating the travel gantry 14 around the rotation axis 18 or the couch drive device 42 so that the therapeutic radiation 23 is transmitted through the three-dimensional position. In this case, the irradiation position control section 58 uses the turning drive device 11 or the traveling drive device for rotating the travel gantry 14 around the rotation axis 18 or the head swing device 15 preferentially prior to the couch drive device 42. Such movement reduces the load of moving the patient 43, which is preferable.

The therapeutic radiation irradiation section 59, after the therapeutic radiation irradiation device 16 is moved by the irradiation position control section 58, irradiates the affected area with the therapeutic radiation 23 by using the therapeutic radiation irradiation device 16.

The radiotherapy device control apparatus 2 can also be formed of a plurality of computers connected together so as to be capable of transmitting information bi-directionally to each other. In this case, the three-dimensional data collection section 51, the treatment planning section 52, the imager position control section 53, the DRR image creation section 54, the transmitted image creation section 55, the reference image creation section 56, the affected area position control section 57, the irradiation position control section 58, and the therapeutic radiation irradiation section 59 are each included in any of the plurality of computers. In this case, a plurality of users can perform radiotherapy related operation at separate places. For example, a computer for the user to create a treatment plan and a computer for another user to operate the radiotherapy device 3 can be provided separately.

The first embodiment of the radiation irradiation method according to the present invention are executed by the radiotherapy system 1, and includes, for one patient 43, operation of creating a treatment plan, a first treatment operation, and a second treatment operation and thereafter.

In the operation of creating a treatment plan, the user first gathers three-dimensional data of an affected area of the patient 43 and a portion around the affected area by using the CT 5, and stores the three-dimensional data in the storage device in association with identification information of the patient 43. The radiotherapy device control apparatus 2, based on the three-dimensional data generated by the CT 5, generates an image indicating the affected area of the patient 43 and organs at the periphery of the affected area. The user looks through the image by using the radiotherapy device control apparatus 2, and identifies the position of the affected area. The user, based on the image, further creates a treatment plan by using the treatment planning section 52, and inputs the treatment plan to the radiotherapy device control apparatus 2. The treatment plan indicates irradiation angles at which the affected area of the patient 43 is irradiated with the therapeutic radiation 23, and the dosage and property of the therapeutic radiation 23 irradiated at each of the irradiation angles. The treatment plan further indicates imaging angles at which the diagnostic X-rays 35 and 36 are irradiated when the therapeutic radiation 23 is irradiated at various irradiation angles. The imaging angles are calculated so that the transmitted images taken by transmitting the diagnostic X-rays 35 and 36 through the patient 43 display the affected area of the patient 43 more precisely. The radiotherapy device control apparatus 2 stores the treatment plan in the storage device in association with the identification information of the patient 43.

In the first treatment operation, the user first fixes the patient 43 to the couch 41 of the radiotherapy device 3 in the same posture as when three-dimensional data is gathered by the CT 5. The radiotherapy device control apparatus 2, based on the three-dimensional data collected in the operation of creating a treatment plan, calculates the DRR image. The DRR image indicates transmitted images taken when the diagnostic X-rays 35 and 36 are irradiated at the imaging angles indicated by the treatment plan. The user, by using the radiotherapy device control apparatus 2, adds a mark to position in the DRR image where a characteristic point of the patient 43 is displayed so that the characteristic point displayed in the DRR image can be recognized. The radiotherapy device control apparatus 2 stores the DRR image in the storage device in association with the identification information of the patient 43.

Next, the radiotherapy device control apparatus 2 executes operation of position adjustment of the patient 43. Specifically, the radiotherapy device control apparatus 2 controls the radiation source drive device 37 to move the diagnostic X-ray source 24 so that the diagnostic X-rays 35 are irradiated to the patient 43 at the imaging angle indicated by the treatment plan, and controls the sensor array drive device 27 to move the sensor array 32 so that the transmitted image obtained by the diagnostic X-rays 35 mainly displays the affected area of the patient 43 in the center. The radiotherapy device control apparatus 2 further controls the radiation source drive device 38 to move the diagnostic X-ray source 25 so that the diagnostic X-rays 36 are irradiated to the patient 43 at the imaging angle indicated by the treatment plan, and controls the sensor array drive device 28 to move the sensor array 33 so that the transmitted image obtained by the diagnostic X-rays 36 mainly displays the affected area of the patient 43 in the center. The radiotherapy device control apparatus 2 further controls the turning drive device 11 or the traveling drive device to move the therapeutic radiation irradiation device 16 so that the therapeutic radiation 23 is irradiated to the patient 43 at the imaging angle indicated by the treatment plan, and controls the sensor array drive device 26 to move the sensor array 31 so that the transmitted image obtained by the therapeutic radiation 23 mainly display the affected area of the patient 43 in the center.

The radiotherapy device control apparatus 2 radiates the diagnostic X-rays 35 by using the diagnostic X-ray source 24 and takes a transmitted image of the patient 43 generated by using the sensor array 32 based on the diagnostic X-rays 35. The radiotherapy device control apparatus 2 further radiates the diagnostic X-rays 36 by using the diagnostic X-ray source 25 and takes a transmitted image of the patient 43 generated by using the sensor array 33 based on the diagnostic X-rays 36. The radiotherapy device control apparatus 2 further radiates the therapeutic radiation 23 by using the therapeutic radiation irradiation device 16 and takes a transmitted image of the patient 43 generated by using the sensor array 31 based on the therapeutic radiation 23. The radiotherapy device control apparatus 2 compares the transmitted image with the DRR image to judge whether or not the affected area of the patient 43 is to be irradiated with the therapeutic radiation 23. The radiotherapy device control apparatus 2 further compares the transmitted image with the DRR image to calculate the couch position of the couch 41. For example, based on a difference between the position of the characteristic point displayed in the transmitted image and the position of the characteristic point displayed in the DRR image, the radiotherapy device control apparatus 2 calculates the direction and distance in and by which the patient 43 is to be moved, and moves the couch 41 based on the direction and the distance. Or, the user controls the couch drive device 42 to move the patient 43 by using the radiotherapy device control apparatus 2 while viewing the display so that the taken transmitted image approximately matches with the DRR image. The radiotherapy device control apparatus 2 stores the taken image in the storage device in association with the identification information of the patient 43.

Next, the radiotherapy device control apparatus 2 repeatedly executes tracking operation and irradiation operation. In the tracking operation, the radiotherapy device control apparatus 2, based on the position of the affected area displayed in the transmitted images taken by the plurality of imager systems, calculates three-dimensional position, and moves the therapeutic radiation irradiation device 16 by using the head swing device 15 so that the therapeutic radiation 23 is transmitted through the three-dimensional position. In the irradiation operation, the radiotherapy device control apparatus 2 irradiates the therapeutic radiation 23 to the affected area by using the therapeutic radiation irradiation device 16. Such tracking operation and irradiation operation permit the radiotherapy device 3 to more reliably irradiate only the affected area moving due to breathing or the like, thus achieving treatment with the higher accuracy.

In the second treatment operation and thereafter, the user first fixes the patient 43 to the couch 41 of the radiotherapy device 3 in the same posture as in the treatment operation executed in the past. The radiotherapy device control apparatus 2 creates a reference image based on the transmitted image photographed in the previous treatment operation. The previous treatment operation indicates treatment operation executed before the current treatment operation, i.e., a first to (n−1)-th treatment operation where the current treatment operation is n-th (n=2, 3, 4, . . . ) operation. The reference image is a transmitted image taken by the radiotherapy device control apparatus 2 when the affected area of the patient 43 is so arranged as to be irradiated with the therapeutic radiation 23. The user adds a mark, by using the radiotherapy device control apparatus 2, to the position in the reference image where a characteristic point of the reference image is displayed so that the characteristic point of the patient 43 displayed in the reference image can be recognized. This radiotherapy device control apparatus 2 stores the reference image in the storage device in association with the identification information of the patient 43.

Next, the radiotherapy device control apparatus 2 executes the operation of position adjustment of the patient 43. Specifically, the radiotherapy device control apparatus 2 controls the radiation source drive device 37 to move the diagnostic X-ray source 24 so that the diagnostic X-rays 35 are irradiated to the patient at the imaging angle indicated by the treatment plan, and controls the sensor array drive device 27 to move the sensor array 32 so that a transmitted image obtained by the diagnostic X-rays 35 mainly displays the affected area of the patient 43 in the center. The radiotherapy device control apparatus 2 further controls the radiation source drive device 38 to move the diagnostic X-ray source 25 so that the diagnostic X-rays 36 are irradiated to the patient at the imaging angle indicated by the treatment plan, and controls the sensor array drive device 28 to move the sensor array 33 so that a transmitted image obtained by the diagnostic X-rays 36 mainly displays the affected area of the patient 43 in the center. The radiotherapy device control apparatus 2 further controls the head swing device 15 to move the therapeutic radiation irradiation device 16 so that the therapeutic radiation 23 is irradiated to the patient at the imaging angle indicated by the treatment plan, and controls the sensor array drive device 26 to move the sensor array 31 so that a transmitted image obtained by the therapeutic radiation 23 mainly displays the affected area of the patient 43 in the center.

The radiotherapy device control apparatus 2 radiates the diagnostic X-rays 35 by using the diagnostic X-ray source 24 and takes a transmitted image of the patient 43 generated by using the sensor array 32 based on the diagnostic X-rays 35. The radiotherapy device control apparatus 2 radiates the diagnostic X-rays 36 by using the ray source 25 and takes a transmitted image of the patient 43 generated by using the sensor array 33 based on the diagnostic X-rays 36. The radiotherapy device control apparatus 2 radiates the therapeutic radiation 23 by using the therapeutic radiation irradiation device 16 and takes a transmitted image of the patient 43 generated by using the sensor array 31 based on the therapeutic radiation 23. The radiotherapy device control apparatus 2 compares the transmitted image with the reference image to judge whether or not the affected area of the patient 43 is to be irradiated with the therapeutic radiation 23. The radiotherapy device control apparatus 2 further compares the transmitted image with the reference image to calculate couch position of the couch 41. For example, the radiotherapy device control apparatus 2, based on a difference between the position of the characteristic point displayed in the transmitted image and the position of the characteristic point displayed in the reference image, calculates the direction and distance in and by which the patient 43 is to be moved, and moves the couch 41 based on the direction and the distance. Or, the user controls the couch drive device 42 to move the patient 43 by using the radiotherapy device control apparatus 2 while viewing the display so that the taken transmitted image approximately matches with reference image. The radiotherapy device control apparatus 2 stores the taken images in the storage device in association with the identification information of the patient 43.

Next, the radiotherapy device control apparatus 2 repeatedly executes tracking operation and irradiation operation. In the tracking operation, the radiotherapy device control apparatus 2, based on the position of the affected area displayed in the transmitted images taken by the plurality of imager systems, calculates three-dimensional position, and moves the therapeutic radiation irradiation device 16 by using the head swing device 15 so that the therapeutic radiation 23 is transmitted through the three-dimensional position. In the irradiation operation, the radiotherapy device control apparatus 2, after the therapeutic radiation irradiation device 16 is moved by the tracking operation irradiates the therapeutic radiation 23 to the affected area by using the therapeutic radiation irradiation device 16.

The DRR image generally differs from the transmitted image in image quality. For example, the DRR image has a resolution of approximately 1 mm/pixel, while the transmitted image generally can provide a resolution of 0.5 mm/pixel or higher. The radiation irradiation method according to the present invention can match the affected area of the patient 43 with predetermined position (for example, the isocenter 19) of the radiotherapy device 3 with higher accuracy by using a transmitted image having a higher resolution than that of the DRR image. Image processing by the computer or the human typically has difficulty in comparing two images of different image qualities, and thus has difficulty in identifying the position of the affected area through comparison between two images of different image qualities. Therefore, the computer or the human requires much time for such comparison, and further has difficulty in obtaining sufficient comparison accuracy.

In the radiation irradiation method according to the present invention, the computer or the human compares two images of the same image quality for adjusting the position of the affected area of the patient 43 to the irradiation position of the therapeutic radiation 23. Thus, the radiation irradiation method according to the present invention can more easily and more quickly compare two images of the same image quality than comparing two images of different image qualities. Thus, with the radiation irradiation method according to the present invention, the radiotherapy device control apparatus 2 can more quickly calculate the positional relationship between the affected area of the patient 43 and the irradiation position of the therapeutic radiation 23 and can quickly calculate the direction and distance in and by which the couch 41 is to be moved. Further, upon comparing the transmitted image with the reference image while viewing the display of the radiotherapy device control apparatus 2, the user can quickly match the affected area of the patient 43 with the predetermined position of the radiotherapy device with higher accuracy.

Typically, the condition and position of the human internal organs change with time. Such a phenomenon is observed remarkably in the trunk in particular. With the radiation irradiation method according to the present invention, the radiotherapy device control apparatus 2 stores in the storage device the three-dimensional data, a treatment plan, a DRR image, and a reference image in association with identification information of the patient 43. Such storing makes it easy to manage the condition, position, and chronological change of the internal organs of the patient 43, which is preferable. The treatment plan may require modification upon extreme change in the condition and position of the internal organs. Such storing permits early evaluation on whether or not the modification of the treatment plan is required based on comparison between the DRR image and the current transmitted image.

The time period from when the operation of creating the treatment plan is executed to when the first treatment operation is executed is generally sufficiently longer than an interval between a plurality of treatment operations executed, and thus the condition and position of the organs possibly change to an extent that disturbs radiotherapy. With the radiation irradiation method according to the present invention, in the second treatment operation and thereafter, the position of the affected area is adjusted by using a reference image indicating the condition and position of the affected area gathered at a shorter time interval than that at the treatment planning (e.g. just before the treatment operation). Thus, in the second treatment operation and thereafter, the affected area of the patient 43 can be quickly matched with predetermined position of the radiotherapy device 3 with higher accuracy. Further, with the radiation irradiation method according to the present invention, the chronological change of the condition and position of the affected area of the patient 43 thereof can be recorded (stored) more precisely, so that the user can judge whether or not to carry out a treatment plan initially set based on the chronological change and thus can more accurately evaluate a treatment calendar based on the chronological change.

Figure 4:
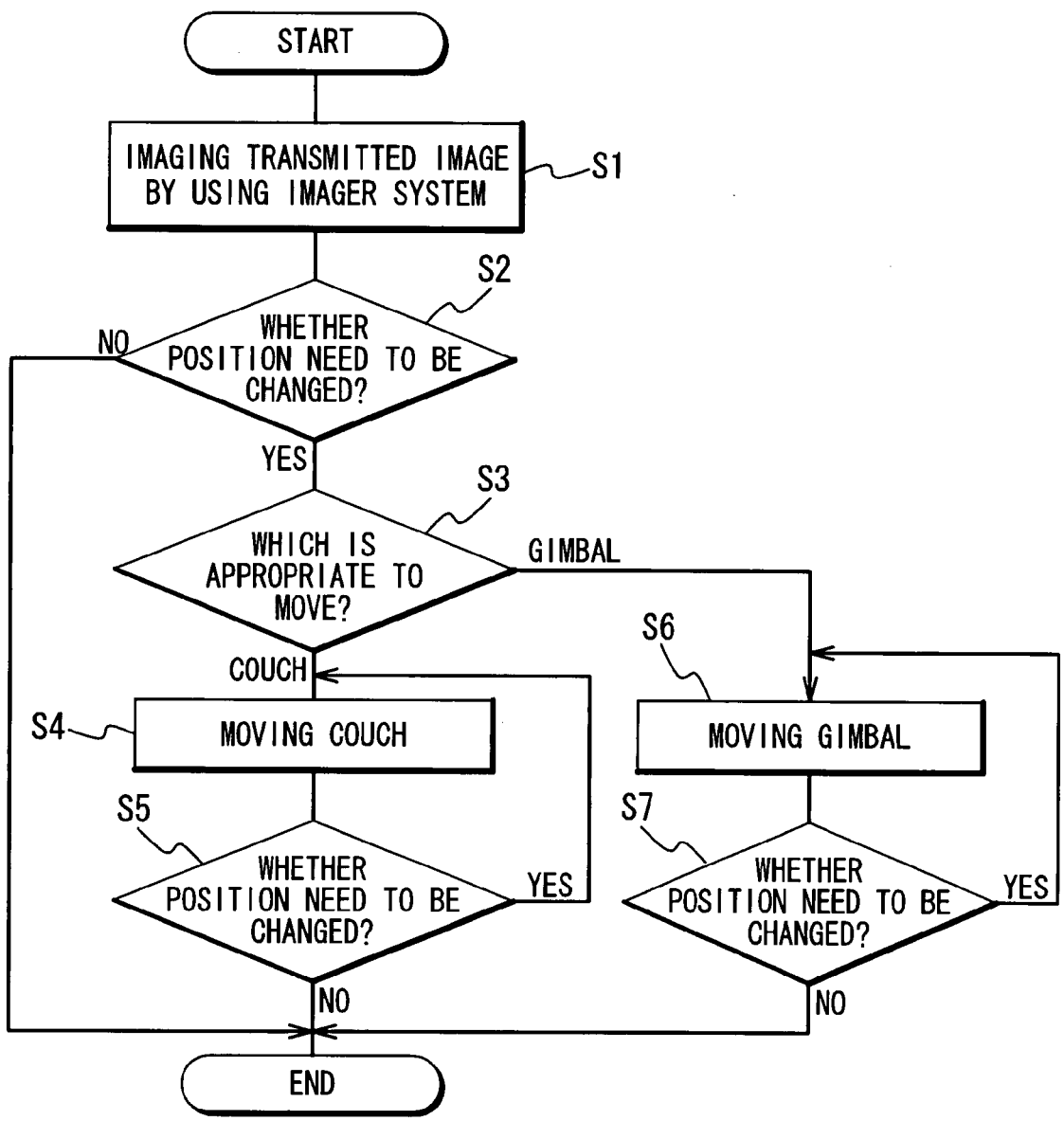
FIG. 4 is a flowchart showing an example of a position adjustment operation in a treatment operation in the embodiment.

FIG. 4 is a flowchart showing an example of the position adjustment operation executed on the patient 43 in the treatment operation in the embodiment. The radiotherapy device control apparatus 2 first takes a transmitted image of the patient 43 by using the imager system (step S1). The radiotherapy device control apparatus 2 calculates the position of an affected area based on the position of a characteristic point displayed in the transmitted image, and calculates an amount of difference between this position and the position where the therapeutic radiation 23 is irradiated. The radiotherapy device control apparatus 2, based on the amount of difference, judges whether or not the relative position between the therapeutic radiation irradiation device 16 and the couch 41 needs to be changed so that the therapeutic radiation 23 is irradiated to the aforementioned position (step S2).

The radiotherapy device control apparatus 2, when the relative position needs to be changed (YES in step S2), judges whether it is appropriate to move the couch 41 or to move the therapeutic radiation irradiation device 16 so that the therapeutic radiation 23 is irradiated to the position (step S3). For example, the radiotherapy device control apparatus 2 selects the couch 41 when the difference is larger than a predetermined value, and selects the therapeutic radiation irradiation device 16 when the difference is smaller than the predetermined value.

The radiotherapy device control apparatus 2, when the couch 41 is selected (couch in step S3), moves the couch 41 by using the couch drive device 42 (step S4) until the difference becomes sufficiently small (NO in step S5). The radiotherapy device control apparatus 2, when the therapeutic radiation irradiation device 16 is selected (gimbal in step S3), moves the therapeutic radiation irradiation device 16 by using the head swing device 15 (step S6) until the difference becomes sufficiently small (NO in step S7). Such position adjustment operation can move the therapeutic radiation irradiation device 16 preferentially prior to the couch 41 (patient 43), thus permitting reducing the burden imposed on the patient 43, which is preferable. Thus, the predetermined value is assumed as, for example, a value which permits the therapeutic radiation 23 to be irradiated to the position of the affected area by the head swing device 15 according to the treatment plan. Moreover, the imager system can perform irradiation more exactly according to the treatment plan by being provided with capability of three-dimensionally recognizing the position of the affected area of the patient 43 and the like based on results of imaging from a plurality of angles by using, for example, the system described above.

Figure 5:
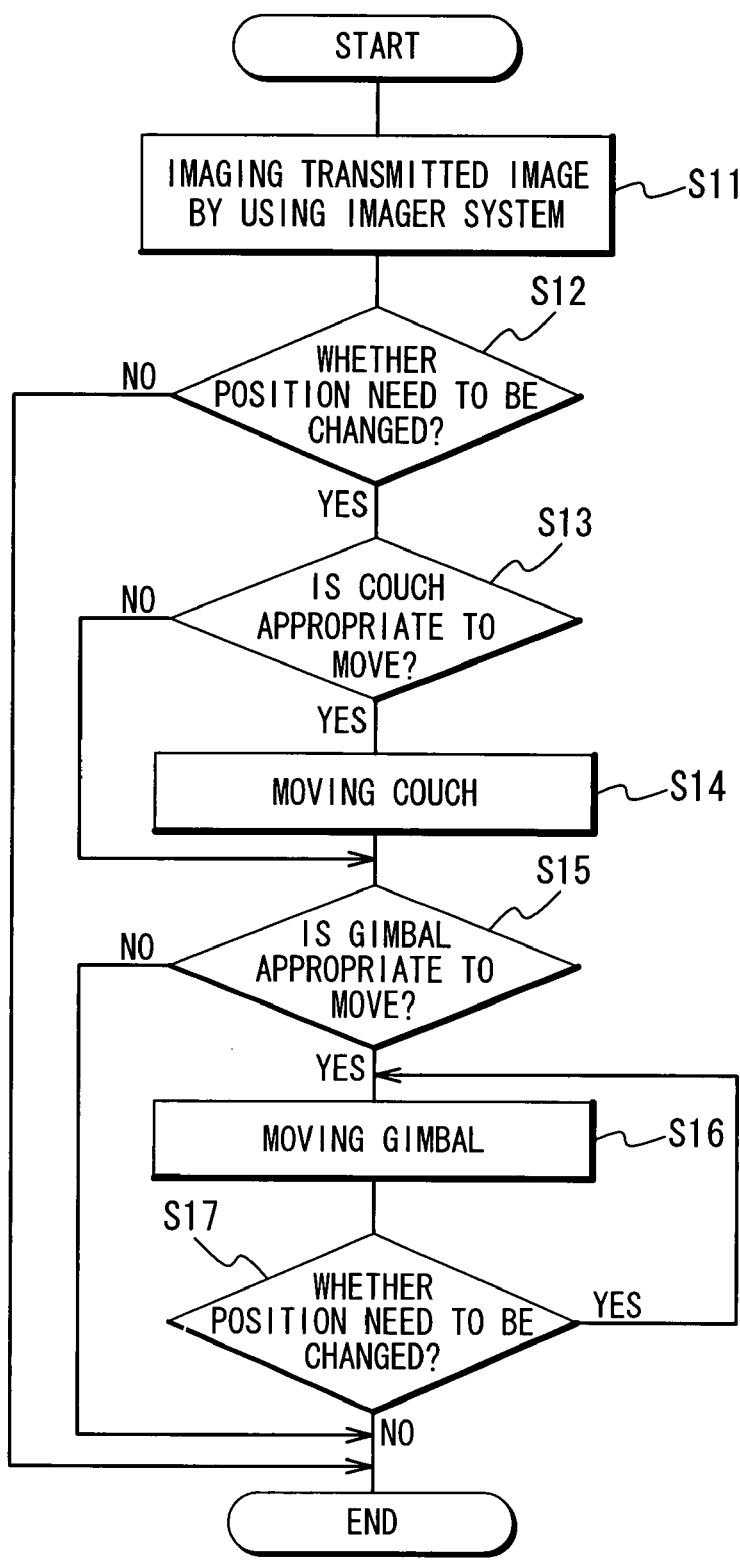
FIG. 5 is a flowchart showing another example of the position adjustment operation executed on the patient in the treatment operation in the embodiment.

FIG. 5 is a flowchart showing another example of the position adjustment operation executed on the patient 43 in the treatment operation in the embodiment. The radiotherapy device control apparatus 2 first takes a transmitted image of the patient 43 by using the imager system (step S11). The radiotherapy device control apparatus 2 calculates the position of an affected area based on the position of a characteristic point displayed in the transmitted image, and calculates an amount of difference between this position and the position where the therapeutic radiation 23 is irradiated. The radiotherapy device control apparatus 2, based on the amount of difference, judges whether or not the relative position between the therapeutic radiation irradiation device 16 and the couch 41 needs to be changed so that the therapeutic radiation 23 is irradiated to the aforementioned position (step S12).

The radiotherapy device control apparatus 2, when the relative position needs to be changed (YES in step S12), judges whether or not the couch 41 needs to be moved (step S13). For example, the radiotherapy device control apparatus 2 judges that the couch 41 needs to be moved when the difference is larger than the predetermined value. The radiotherapy device control apparatus 2, when the couch 41 needs to be moved (YES in step S13), moves the couch 41 by using the couch drive device 42 so that the difference becomes sufficiently small (step S14).

The radiotherapy device control apparatus 2, when the couch 41 needs not to be moved (NO in step S13) or after the couch 41 is moved, judges whether or not the therapeutic radiation irradiation device 16 needs to be moved so that the therapeutic radiation 23 is transmitted through the three-dimensional position (step S15). The radiotherapy device control apparatus 2, when the therapeutic radiation irradiation device 16 needs to be moved (YES in step S15), moves the therapeutic radiation irradiation device 16 by using the head swing device 15 (step S16) so that a difference between the position of the affected area and the position through which the therapeutic radiation 23 is transmitted becomes sufficiently small (NO in step S17). Such position adjustment operation is preferable in that it can move the therapeutic radiation irradiation device 16 preferentially prior to the couch 41 (patient 43) thereby reducing the burden imposed on the patient 43 and also preferable in that the both functions can be used in a mutually complementary manner. The predetermined value and the imager system configuration are the same as those in the previous example. The couch drive device 42 generally has a lower accuracy in position adjustment than the head swing device 15. Thus, there is a concern that, in the position adjustment operation of FIG. 4, in the event of shift to a degree equal to or greater than a certain value, only the couch 41 is moved and thus the irradiation position slightly shifts. In the position adjustment operation of FIG. 5, after the couch 41 is moved, position adjustment is further performed by the head swing device 15, thus permitting position adjustment with the higher accuracy than that achieved by the flow of FIG. 4.

A modified embodiment of the radiotherapy device control apparatus 2 according to the present invention is further provided with the three-dimensional data creation section 65 shown in FIG. 3 as a computer program. The three-dimensional data creation section 65, while rotating the travel gantry 14 around the rotation axis 18 by using the traveling drive device of the radiotherapy device 3, generates a plurality of transmitted images of the patient 43 generated by transmitting X-rays through the human body from various directions by using the therapeutic radiation irradiation device 16 and the sensor array 31 of the radiotherapy device 3. The three-dimensional data creation section 65 subjects the plurality of transmitted images to image processing by the computer to thereby generate images of cross sections of the human bodies and then generate three-dimensional data indicating inner condition of the human body. Such image processing is well known. The three-dimensional data creation section 65, while rotating the travel gantry 14 around the rotation axis 18 by using the traveling drive device of the radiotherapy device 3, can also generate a plurality of transmitted images of the patient 43 generated by transmitting X-rays through the human body from various directions by using the diagnostic X-ray source 24 and the sensor array 32 of the radiotherapy device 3. The three-dimensional data creation section 65 subjects the plurality of transmitted images to image processing by the computer to thereby generate images of cross sections of the human body and generate three-dimensional data indicating inner condition of the human body.

A modified embodiment of the radiation irradiation method according to the present invention is executed by a radiotherapy system 1 to which such radiotherapy device control apparatus is applied, with the operation of creating a treatment plan replaced with different operation and the first treatment operation replaced with different operation in the aforementioned radiation irradiation method.

In the operation of creating a treatment plan, the user first fixes the patient 43 to the couch 41 of the radiotherapy device 3 and gathers the three-dimensional data of an affected area of the patient 43 and a portion at the periphery of the affected area by using the therapeutic radiation irradiation device 16 and the sensor array 31 (or the diagnostic X-ray source 24 and the sensor array 32). The radiotherapy device control apparatus 2, based on the three-dimensional data, generates an image indicating the affected area of the patient 43 and organs at the periphery of the affected area. The user looks through the image by using the radiotherapy device control apparatus 2 to identify the position of the affected area. The user, based on the image, further creates a treatment plan and inputs the treatment plan to the radiotherapy device control apparatus 2. The treatment plan indicates irradiation angles at which the therapeutic radiation 23 is irradiated to the affected area of the patient 43 and the dosage and condition of the therapeutic radiation 23 irradiated at the irradiation angles. The treatment plan further indicates imaging angles at which the diagnostic X-rays 35 and 36 are irradiated upon the irradiation of the therapeutic radiation 23 at the irradiation angles.

In the first treatment operation, the user first fixes the patient 43 to the couch 41 of the radiotherapy device 3 in the same posture as when the three-dimensional data has been gathered. The radiotherapy device control apparatus 2, based on a transmitted image taken in the operation of creating a treatment plan, creates a reference image. The transmitted image is an image used to generate the three-dimensional data indicating the inner condition of the patient 43. The user, by using the radiotherapy device control apparatus 2, adds a mark to the position in the reference image where the characteristic point of the patient 43 is displayed so that the characteristic point of the patient 43 displayed in the reference image can be recognized.

The radiotherapy device control apparatus 2 controls the radiation source drive device 37 to move the diagnostic X-ray source 24 so that the diagnostic X-rays 35 are irradiated to the patient 43 at the imaging angle indicated by the treatment plan, and controls the sensor array drive device 27 to move the sensor array 32 so that the transmitted image obtained by the diagnostic X-rays 35 mainly displays the affected area of the patient 43 in the center. The radiotherapy device control apparatus 2 further controls the radiation source drive device 38 to move the diagnostic X-ray source 25 so that the diagnostic X-rays 36 are irradiated to the patient 43 at the imaging angle indicated by the treatment plan, and controls the sensor array drive device 28 to move the sensor array 33 so that the transmitted image obtained by the diagnostic X-rays 36 mainly displays the affected area of the patient 43 in the center. The radiotherapy device control apparatus 2 further controls the head swing device 15 to move the therapeutic radiation irradiation device 16 so that the therapeutic radiation 23 is irradiated to the patient 43 at the imaging angle indicated by the treatment plan, and controls the sensor array drive device 26 to move the sensor array 31 so that the transmitted image obtained by the therapeutic radiation 23 mainly displays the affected area of the patient 43 in the center.

The radiotherapy device control apparatus 2 radiates the diagnostic X-rays 35 by using the diagnostic X-ray source 24 and takes a transmitted image of the patient 43 generated by using the sensor array 32 based on the diagnostic X-rays 35. The radiotherapy device control apparatus 2 radiates the diagnostic X-rays 36 by using the diagnostic X-ray source 25 and takes a transmitted image of the patient 43 generated by using the sensor array 33 based on the diagnostic X-rays 36. The radiotherapy device control apparatus 2 radiates the therapeutic radiation 23 by using the therapeutic radiation irradiation device 16 and takes a transmitted image of the patient 43 generated by using the sensor array 31 based on the therapeutic radiation 23. The radiotherapy device control apparatus 2 compares the transmitted image with the reference image, and moves the couch 41 so that the affected area of the patient 43 matches with predetermined position of the radiotherapy device 3. For example, the radiotherapy device control apparatus 2 calculates a difference between the position of a characteristic point displayed in the transmitted image and the position of a characteristic point displayed in the reference image. The radiotherapy device control apparatus 2, based on the difference, calculates the direction and distance in and by which the patient 43 is to be moved, and moves the couch 41 based on the direction and the distance.

Next, the radiotherapy device control apparatus 2 repeatedly executes tracking operation and irradiation operation. In the tracking operation, the radiotherapy device control apparatus 2, based on the position of the affected area displayed in the transmitted images taken by the plurality of imager systems, calculates three-dimensional position of the affected area, and moves the therapeutic radiation irradiation device 16 by using the head swing device 15 so that the therapeutic radiation 23 is transmitted through the three-dimensional position. In the irradiation operation, the radiotherapy device control apparatus 2 irradiates the therapeutic radiation 23 to the affected area by using the therapeutic radiation irradiation device 16. With such tracking operation and irradiation operation, the radiotherapy device 3 can more reliably irradiate only the affected area which moves due to breathing or the like, thus achieving treatment with the higher accuracy.

Such a radiation irradiation method can, for position adjustment, refer to an image having higher resolution than that of the DRR image even in the first treatment operation, and can match the affected area of the patient 43 with predetermined position of the radiotherapy device 3 (for example, the isocenter 19) with the higher accuracy. Further, with such a radiation irradiation method, the radiotherapy system 1 is no longer required to be provided with the CT 5, and thus can be installed in smaller space and also can be manufactured at lower costs.

In another modified embodiment of the imager position control section according to the present invention, the imager position control section 53 and the transmitted image creation section 55 have functions different from the above-described embodiment.

In this case, the imager position control section 53 controls the turning drive device 11 or the head swing device 15 or the traveling drive device for rotating the travel gantry 14 around the rotation axis 18 to move the therapeutic radiation irradiation device 16 so that the therapeutic radiation 23 is irradiated to the patient 43 at an imaging angle indicated by the treatment plan created by the treatment planning section 52, and controls the sensor array drive device 26 to move the sensor array 31 so that a transmitted image obtained by the therapeutic radiation 23 mainly displays the affected area of the patient 43 in the center.

The transmitted image creation section 55, after the therapeutic radiation irradiation device 16 is moved by the imager position control section 53 and then the sensor array 31 moves, radiates the therapeutic radiation 23 by using the therapeutic radiation irradiation device 16 and takes a transmitted image of the patient 43 generated by using the sensor array 31 based on the therapeutic radiation 23.

Such a radiotherapy device control apparatus 2, as is the case with the radiotherapy device control apparatus 2 in the embodiment already described, can control the radiotherapy device 3 so that the therapeutic radiation 23 is irradiated to the affected area of the patient 43. In this case, the radiotherapy device 3 no longer requires the radiation source drive devices 37 and 38, the diagnostic X-ray sources 24 and 25, the sensor array drive devices 27 and 28, and the sensor arrays 32 and 33. The radiotherapy device 3, when not provided with the radiation source drive devices 37 and 38, the diagnostic X-ray sources 24 and 25, the sensor array drive devices 27 and 28, and the sensor arrays 32 and 33, can be manufactured at a lower price, which is preferable.

It is apparent that the present invention is not limited to the above embodiment, that may be modified and changed without departing from the scope and spirit of the invention.

What is claimed is:

1. A radiotherapy device control apparatus for controlling a radiotherapy device,
    wherein the radiotherapy device includes:
    a therapeutic radiation irradiation device which radiates therapeutic radiation, an imager which generates an imager image of a subject by using radiation transmitted through the subject,
    a table on which the subject is arranged, and
    a drive device which moves a relative position of the table with respect to the therapeutic radiation irradiation device, said radiotherapy device control apparatus comprising:
    a reference image creation section;
    a transmitted image creation section;
    an affected area position control section;
    a three-dimensional data obtaining section which obtains three-dimensional data of the subject; and
    a two-dimensional image creation section which creates a two-dimensional image based on the three-dimensional data,
    wherein said reference image creation section collects a reference imager image taken by the imager,
    wherein said transmitted image creation section takes a transmitted imager image of the subject by the imager,
    wherein said affected area position control section, in a first treatment operation, judges whether or not the relative position of the table with respect to the therapeutic radiation irradiation device is appropriate based on a third position at which a characteristic point of the subject is displayed in the transmitted imager image and a fourth position at which the characteristic point is displayed in the two-dimensional image, and changes the relative position of the table by using the drive device based on the third position and the fourth position, and
    wherein said affected area position control section, in a second treatment operation and thereafter, judges whether or not the relative position of the table with respect to the therapeutic radiation irradiation device is appropriate based on a first position at which the characteristic point of the subject is displayed in the transmitted imager image and a second position at which the characteristic point is displayed in the reference imager image, which includes the transmitted imager image taken at a previous treatment operation, and
    changes the relative position of the table by using the drive device based on the first position and the second position.

2. The radiotherapy device control apparatus according to claim 1, wherein the imager takes the reference imager image when a part of the subject is arranged to be irradiated with the therapeutic radiation, and wherein said affected area position control section, when a first relative position coincides with a second relative position, changes the relative position of the table by using the drive device such that the first position coincides with the second position, the first relative position is a relative position of the imager with respect to the therapeutic radiation irradiation device when the transmitted imager image is taken, and the second relative position is a relative position of the imager with respect to the therapeutic radiation irradiation device when the reference imager image is taken.

3. The radiotherapy device control apparatus according to claim 1, wherein said affected area position control section, based on a relation between the second position and a part position of a part of the subject, changes the relative position of the table by using the drive device such that the part position calculated by using the first position is irradiated with the therapeutic radiation.

4. The radiotherapy device control apparatus according to claim 3, wherein the drive device includes:
a table drive device which moves the table, and
an irradiation drive device which moves the therapeutic radiation irradiation device,
wherein said affected area position control section changes the relative position of the table using the irradiation drive device.

5. The radiotherapy device control apparatus according to claim 4, wherein the imager includes:
a first imager, and
a second imager,
wherein the reference imager image includes:
a first reference imager image which is taken by the first imager, and
a second reference imager image which is taken by the second imager,
wherein the transmitted imager image includes:
a first transmitted imager image which is taken by the first imager, and
a second transmitted imager image which is taken by the second imager,
wherein said affected area position control section changes the relative position of the table by using the drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and a sixth position at which the characteristic point is displayed in the second reference imager image.

6. The radiotherapy device control apparatus according to claim 4, wherein the imager includes:
a radiation imager which generates at least one of the transmitted imager image and the reference imager image by using the therapeutic radiation.

7. The radiotherapy device control apparatus according to claim 4, wherein said three-dimensional data obtaining section includes:
a three-dimensional data creation section which creates the three-dimensional data of the subject based on a transmitted image taken by the imager.

8. The radiotherapy device control apparatus according to claim 4, wherein said three-dimensional data obtaining section includes:
a three-dimensional data collection section which collects the three-dimensional data of the subject, the three-dimensional data being created by a three-dimensional imaging device provided in addition to the radiotherapy device.

9. The radiotherapy device control apparatus according to claim 3, wherein the imager includes:
a first imager, and
a second imager,
wherein the reference imager image includes:
a first reference imager image which is taken by the first imager, and
a second reference imager image which is taken by the second imager,
wherein the transmitted imager image includes:
a first transmitted imager image which is taken by the first imager, and
a second transmitted imager image which is taken by the second imager,
wherein said affected area position control section changes the relative position of the table by using the drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and a sixth position at which the characteristic point is displayed in the second reference imager image.

10. The radiotherapy device control apparatus according to claim 3, wherein the imager includes:
a radiation imager which generates at least one of the transmitted imager image and the reference imager image by using the therapeutic radiation.

11. The radiotherapy device control apparatus according to claim 3, wherein said three-dimensional data obtaining section includes:
a three-dimensional data creation section which creates the three-dimensional data of the subject based on a transmitted image taken by the imager.

12. The radiotherapy device control apparatus according to claim 3, wherein said three-dimensional data obtaining section includes:
a three-dimensional data collection section which collects the three-dimensional data of the subject, the three-dimensional data being created by a three-dimensional imaging device provided in addition to the radiotherapy device.

13. The radiotherapy device control apparatus according to claim 1, wherein the imager is rotatable around a pan axis parallel to a main direction of the table, and around a tilt axis perpendicular to the pan axis.

14. A radiotherapy system comprising:
a radiotherapy device control apparatus; and
a radiotherapy device,
wherein said radiotherapy device control apparatus includes:
a reference image creation section;
a transmitted image creation section;
an affected area position section;
a three-dimensional data obtaining section which obtains three-dimensional data of the subject; and
a two-dimensional image creation section which creates a two-dimensional image based on the three-dimensional data,
wherein said radiotherapy device control apparatus controls said radiotherapy device, wherein said radiotherapy device includes:
a therapeutic radiation irradiation device which radiates therapeutic radiation,
an imager which generates an imager image of a subject by using radiation transmitted through the subject,
a table on which the subject is arranged, and
a drive device which moves a relative position of said table, with respect to said therapeutic radiation irradiation device,
wherein said reference image creation section collects a reference imager image taken by said imager,
wherein said transmitted image creation section takes a transmitted imager image of the subject by said imager,
wherein said affected area position control section, in a first treatment operation, judges whether or not the relative position of said table with respect to said therapeutic radiation irradiation device is appropriate based on a third position at which a characteristic point of the subject is displayed in the transmitted imager image and a fourth position at which the characteristic point is displays in the two-dimensional image, and changes the relative position of said table by using said drive device based on the third position and the fourth position, and
wherein said affected area position control section, in a second treatment operation and thereafter, judges whether or not the relative position of said table with respect to said therapeutic radiation irradiation device is appropriate based on a first position at which a characteristic point of the subject is displayed in the transmitted imager image and a second position at which the characteristic point is displayed in the reference imager image, which includes the transmitted imager image taken at a previous treatment operation, and changes the relative position of said table by using said drive device based on the first position and the second position.

15. The radiotherapy system according to claim 14, wherein said imager takes the reference imager image when a part of the subject is arranged to be irradiated with the therapeutic radiation, and
wherein said affected area position control section, when a first relative position coincides with a second relative position, changes the relative position of said table by using said drive device such that the first position coincides with the second position, the first relative position is a relative position of said imager with respect to said therapeutic radiation irradiation device when the transmitted imager image is taken, and the second relative position is a relative position of said imager with respect to said therapeutic radiation irradiation device when the reference imager image is taken.

16. The radiotherapy system according to claim 14, wherein said affected area position control section, based on a relation between the second position and a part position of a part of the subject, changes the relative position of said table by using said drive device such that the part position calculated by using the first position is irradiated with the therapeutic radiation.

17. The radiotherapy system according to claim 16, wherein said drive device includes:
a table drive device which moves said table, and
an irradiation drive device which moves said therapeutic radiation irradiation device,
wherein said affected area position control section changes the relative position of said table using said irradiation drive device.

18. The radiotherapy system according to claim 17, wherein said imager includes:
a first imager, and
a second imager,
wherein the reference imager image includes:
a first reference imager image which is taken by said first imager, and
a second reference imager image which is taken by said second imager,
wherein the transmitted imager image includes:
a first transmitted imager image which is taken by said first imager, and
a second transmitted imager image which is taken by said second imager,
wherein said affected area position control section changes the relative position of said table by using said drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and sixth position at which the characteristic point is displayed in the second reference imager image.

19. The radiotherapy system according to claim 17, wherein said imager includes:
a radiation imager which generates at least one of the transmitted imager image and the reference imager image by using the therapeutic radiation.

20. The radiotherapy system according to claim 17, wherein said three-dimensional data obtaining section includes:
a three-dimensional data creation section which creates the three-dimensional data of the subject based on a transmitted image taken by said imager.

21. The radiotherapy system according to claim 17, wherein said three-dimensional data obtaining section includes:
a three-dimensional data collection section which collects the three-dimensional data of the subject, the three-dimensional data is created by a three-dimensional imaging device provided in addition to said radiotherapy device.

22. The radiotherapy system according to claim 16, wherein said imager includes:
a first imager, and
a second imager,
wherein the reference imager image includes:
a first reference imager image which is taken by said first imager, and
a second reference imager image which is taken by said second imager,
wherein the transmitted imager image includes:
a first transmitted imager image which is taken by said first imager, and
a second transmitted imager image which is taken by said second imager,
wherein said affected area position control section changes the relative position of said table by using said drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and a sixth position at which the characteristic point is displayed in the second reference imager image.

23. The radiotherapy system according to claim 16, wherein said imager includes:
a radiation imager which generates at least one of the transmitted imager image and the reference imager image by using the therapeutic radiation.

24. The radiotherapy system according to claim 16, wherein said three-dimensional data obtaining section includes:
a three-dimensional data creation section which creates the three-dimensional data of the subject based on a transmitted image taken by said imager.

25. The radiotherapy system according to claim 16, wherein said three-dimensional data obtaining section includes:
a three-dimensional data collection section which collects the three-dimensional data of the subject, the three-dimensional data is created by a three-dimensional imaging device provided in addition to said radiotherapy device.

26. The radiotherapy system according to claim 14, wherein said imager is rotatable around a pan axis parallel to a main direction of the table, and around a tilt axis perpendicular to the pan axis.

27. A radiation irradiation method using a radiotherapy device, wherein the radiotherapy device includes:
a therapeutic radiation irradiation device which radiates therapeutic radiation,
an imager which generates an imager image of a subject by using radiation transmitted through the subject,
a table on which the subject is arranged, and
a drive device which moves a relative position of the table, with respect to the therapeutic radiation irradiation device,
said radiation irradiation method comprising:
obtaining three-dimensional data of the subject;
creating a two-dimensional image based on the three-dimensional data;
taking a transmitted imager image of the subject by the imager in a first treatment operation;
judging whether or not the relative position of the table with respect to the therapeutic radiation irradiation device is appropriate based on a third position at which a characteristic point of the subject is displayed in the transmitted imager image and a fourth position at which the characteristic point is displayed in the two-dimensional image, in the first treatment operation;
changing the relative position of the table by using the drive device based on the third position and the fourth position, in the first treatment operation;
collecting a reference imager image, which includes the transmitted imager image taken by the imager at a previous treatment operation;
imaging a transmitted imager image of the subject by the imager, in a second treatment operation and thereafter;
judging whether or not the relative position of the table with respect to the therapeutic radiation irradiation device is appropriate based on a first position at which the characteristic point of the subject is displayed in the transmitted imager image and a second position at which the characteristic point is displayed in the reference imager image, in the second treatment operation and thereafter; and
changing the relative position of the table by using the drive device based on the first position and the second position, in the second treatment operation and thereafter.

28. The radiation irradiation method according to claim 27, wherein the reference imager image is taken by the imager when a part of the subject is arranged to be irradiated with the therapeutic radiation, and
wherein said changing, in the second treatment operation and thereafter, comprises changing the relative position of the table by using the drive device when a first relative position coincides with a second relative position such that the first position coincides with the second position, the first relative position is a relative position of the imager with respect to the therapeutic radiation irradiation device when the transmitted imager image is taken, and the second relative position is a relative position of the imager with respect to the therapeutic radiation irradiation device when the reference imager image is taken.

29. The radiation irradiation method according to claim 27, wherein said changing, in the second treatment operation and thereafter, comprises changing the relative position of the table by using the drive device based on a relation between the second position and a part position of a part of the subject such that the part position calculated by using the first position is irradiated with the therapeutic radiation.

30. The radiation irradiation method according to claim 29, wherein the drive device includes:
a table drive device which moves the table, and
an irradiation drive device which moves the therapeutic radiation irradiation device,
wherein the irradiation drive device is used when the relative position of the table is changed.

31. The radiation irradiation method according to claim 30, wherein the imager includes:
a first imager, and
a second imager,
wherein the reference imager image includes:
a first reference imager image which is taken by the first imager, and
a second reference imager image which is taken by the second imager,
wherein the transmitted imager image includes:
a first transmitted imager image which is taken by the first imager, and
a second transmitted imager image which is taken by the second imager, and
wherein said changing comprises changing the relative position of the table by using the drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and a sixth position at which the characteristic point is displayed in the second reference imager image.

32. The radiation irradiation method according to claim 30, wherein the imager includes:
a radiation imager which generates at least one of the transmitted imager image and the reference imager image by using the therapeutic radiation.

33. The radiation irradiation method according to claim 30, wherein said obtaining includes:
creating the three-dimensional data of the subject based on a transmitted image taken by the imager.

34. The radiation irradiation method according to claim 30, wherein said obtaining includes:
collecting the three-dimensional data of the subject, the three-dimensional data being created by a three-dimensional imaging device provided in addition to the radiotherapy device.

35. The radiation irradiation method according to claim 29, wherein the imager includes:
a first imager, and
a second imager,
wherein the reference imager image includes:
a first reference imager image which is taken by the first imager, and
a second reference imager image which is taken by the second imager,
wherein the transmitted imager image includes:
a first transmitted imager image which is taken by the first imager, and
a second transmitted imager image which is taken by the second imager, and
wherein said changing comprises changing the relative position of the table by using the drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and a sixth position at which the characteristic point is displayed in the second reference imager image.

36. The radiation irradiation method according to claim 29, wherein the imager includes:
a radiation imager which generates at least one of the transmitted imager image and the reference imager image by using the therapeutic radiation.

37. The radiation irradiation method according to claim 29, wherein said obtaining includes:
creating the three-dimensional data of the subject based on a transmitted image taken by the imager.

38. The radiation irradiation method according to claim 29, wherein said obtaining includes:
collecting the three-dimensional data of the subject, the three-dimensional data being created by a three-dimensional imaging device provided in addition to the radiotherapy device.

39. The radiation irradiation method according to claim 27, wherein the imager is rotatable around a pan axis parallel to a main direction of the table, and around a tilt axis perpendicular to the pan axis.

40. A computer-readable storage medium having embodied thereon computer program product for implementing a radiation irradiation method using a radiotherapy device, wherein the radiotherapy device includes:
a therapeutic radiation irradiation device which radiates therapeutic radiation,
an imager which generates an imager image of a subject by using radiation transmitted through the subject,
a table on which the subject is arranged, and
a drive device which moves a relative position of the table with respect to the therapeutic radiation irradiation device,
the computer program product comprising code that, when executed, causes a computer to perform:
obtaining three-dimensional data of the subject;
creating a two-dimensional image based on the three-dimensional data;
taking a transmitted imager image of the subject by the imager in a first treatment operation;
judging whether or not the relative position of the table with respect to the therapeutic radiation irradiation device is appropriate based on a third position at which a characteristic point of the subject is displayed in the transmitted imager image and a fourth position at which the characteristic point is displayed in the two-dimensional image, in the first treatment operation;
changing the relative position of the table by using the drive device based on the third position and the fourth position, in the first treatment operation;
collecting a reference imager image, which includes the transmitted imager image taken by the imager at a previous treatment operation;
imaging a transmitted imager image of the subject by the imager, in a second treatment operation and thereafter;
judging whether or not the relative position of the table with respect to the therapeutic radiation irradiation device is appropriate based on a first position at which the characteristic point of the subject is displayed in the transmitted imager image and a second position at which the characteristic point is displayed in the reference imager image, in the second treatment operation and thereafter; and
changing the relative position of the table by using the drive device based on the first position and the second position, in the second treatment operation and thereafter.

41. The computer-readable storage medium according to claim 40, wherein the reference imager image is taken by the imager when a part of the subject is arranged to be irradiated with the therapeutic radiation, and
wherein said changing, in the second treatment operation and thereafter, comprises changing the relative position of the table by using the drive device when a first relative position coincide with a second relative position such that the first position coincides with the second position, the first relative position is a relative position of the imager with respect to the therapeutic radiation irradiation device when the transmitted imager image is taken, and the second relative position is a relative position of the imager with respect to the therapeutic radiation irradiation device when the reference imager image is taken.

42. The computer-readable storage medium according to claim 40, wherein said changing, in the second treatment operation and thereafter, comprises changing the relative position of the table by using the drive device based on a relation between the second position and a part position of a part of the subject such that the part position calculated by using the first position is irradiated with the therapeutic radiation.

43. The computer-readable storage medium according to claim 42, wherein the drive device includes:
a table drive device which moves the table, and
an irradiation drive device which moves the therapeutic radiation irradiation device,
wherein the irradiation drive device is used when the relative position of the table is changed.

44. The computer-readable storage medium according to claim 43, wherein the imager includes:
a first imager, and
a second imager,
wherein the reference imager image includes:
a first reference imager image which is taken by the first imager, and
a second reference imager image which is taken by the second imager, wherein the transmitted imager image includes:
a first transmitted imager image which is taken by the first imager, and
a second transmitted imager image which is taken by the second imager, and
wherein said changing comprises
changing the relative position of the table by using the drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and a sixth position at which the characteristic point is displayed in the second reference imager image.

45. The computer-readable storage medium according to claim 43, wherein the imager includes:
a radiation imager which generates at least one of the transmitted imager image and the reference imager image by using the therapeutic radiation.

46. The computer-readable storage medium according to claim 43, wherein said obtaining includes:
creating the three-dimensional data of the subject based on a transmitted image taken by the imager.

47. The computer-readable storage medium according to claim 43, wherein said obtaining includes:
collecting the three-dimensional data of the subject, the three-dimensional data being created by a three-dimensional imaging device provided in addition to the radiotherapy device.

48. The computer-readable storage medium according to claim 42, wherein the imager includes:
a first imager, and
a second imager,
wherein the reference imager image includes:
a first reference imager image which is taken by the first imager, and
a second reference imager image which is taken by the second imager,
wherein the transmitted imager image includes:
a first transmitted imager image which is taken by the first imager, and
a second transmitted imager image which is taken by the second imager, and
wherein said changing comprises
changing the relative position of the table by using the drive device based on a seventh position at which the characteristic point of the subject is displayed in the first transmitted imager image, an eighth position at which the characteristic point is displayed in the first reference imager image, a fifth position at which the characteristic point of the subject is displayed in the second transmitted imager image, and a sixth position at which the characteristic point is displayed in the second reference imager image.

49. The computer-readable storage medium according to claim 42, wherein the imager includes:
a radiation imager which generates at least one of the transmitted imager image and the reference imager image by using the therapeutic radiation.

50. The computer-readable storage medium according to claim 42, wherein said obtaining includes:
creating the three-dimensional data of the subject based on a transmitted image taken by the imager.

51. The computer-readable storage medium according to claim 42, wherein said obtaining includes:
collecting the three-dimensional data of the subject, the three-dimensional data being created by a three-dimensional imaging device provided in addition to the radiotherapy device.

52. The computer-readable storage medium according to claim 40, wherein the imager is rotatable around a pan axis parallel to a main direction of the table, and around a tilt axis perpendicular to the pan axis.

* * * * *